(12) United States Patent
Lagrange

(10) Patent No.: US 7,497,878 B2
(45) Date of Patent: Mar. 3, 2009

(54) AZO DYES CONTAINING A SULPHONAMIDE OR AMIDE FUNCTION FOR THE DYEING OF HUMAN KERATIN FIBERS AND METHOD OF DYEING AND DYEING COMPOSITIONS CONTAINING THEM

(75) Inventor: Alain Lagrange, Coupvray (FR)

(73) Assignee: L'Oreal, S.A., Paris (FR)

( * ) Notice: Subject to any disclaimer, the term of this patent is extended or adjusted under 35 U.S.C. 154(b) by 201 days.

(21) Appl. No.: 11/477,381

(22) Filed: Jun. 30, 2006

(65) Prior Publication Data

US 2007/0011830 A1    Jan. 18, 2007

Related U.S. Application Data

(60) Provisional application No. 60/785,986, filed on Mar. 27, 2006.

(30) Foreign Application Priority Data

Jun. 30, 2005    (FR) .................................. 05 51843

(51) Int. Cl.
*A61Q 5/10* (2006.01)
*C07D 277/62* (2006.01)

(52) U.S. Cl. ........................ 8/405; 8/406; 8/407; 8/409; 8/435; 8/437; 8/455; 8/565; 8/566; 8/567; 8/568; 8/570; 8/573; 548/152

(58) Field of Classification Search .................... 8/405, 8/406, 407, 409, 435, 437, 455, 565, 566, 8/567, 568, 570, 573; 548/152

See application file for complete search history.

(56) References Cited

U.S. PATENT DOCUMENTS

| | | | |
|---|---|---|---|
| 3,360,508 A | 12/1967 | Sureau et al. | |
| 3,417,075 A | 12/1968 | Mingasson et al. | |
| 3,455,898 A | 7/1969 | Seefelder et al. | |
| 3,562,245 A | 2/1971 | Mohr et al. | |
| 3,585,182 A | 6/1971 | Straley et al. | |
| 3,826,800 A | 7/1974 | Dehnert et al. | |
| 3,985,499 A | 10/1976 | Lang et al. | |
| 4,003,699 A | 1/1977 | Rose et al. | |
| 4,006,127 A | 2/1977 | Raue et al. | |
| 4,082,740 A | 4/1978 | Mohr et al. | |
| 5,061,289 A | 10/1991 | Clausen et al. | |
| 5,208,325 A | 5/1993 | Berneth et al. | |
| 5,380,340 A | 1/1995 | Neunhoeffer et al. | |
| 5,446,136 A * | 8/1995 | Pape et al. ................. | 534/753 |
| 5,534,267 A | 7/1996 | Neunhoeffer et al. | |
| 5,580,964 A | 12/1996 | Berneth et al. | |
| 5,663,366 A | 9/1997 | Neunhoeffer et al. | |
| 5,708,151 A | 1/1998 | Möckli | |
| 5,733,343 A | 3/1998 | Möckli | |
| 5,766,576 A | 6/1998 | Löwe et al. | |
| 5,888,252 A | 3/1999 | Möckli | |
| 5,952,475 A | 9/1999 | Berneth | |
| 5,993,490 A | 11/1999 | Rondeau et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,077,873 B2 | 7/2006 | David et al. | |
| 7,087,096 B2 | 8/2006 | Rondeau | |
| 2002/0007521 A1* | 1/2002 | Lang et al. ..................... | 8/405 |
| 2002/0050013 A1 | 5/2002 | Vidal et al. | |
| 2002/0095732 A1 | 7/2002 | Kravtchenko et al. | |
| 2003/0019051 A9 | 1/2003 | Vidal et al. | |
| 2003/0084516 A9 | 5/2003 | Kravtchenko et al. | |
| 2003/0106169 A1 | 6/2003 | Vidal et al. | |
| 2004/0093675 A1 | 5/2004 | Vidal et al. | |

(Continued)

FOREIGN PATENT DOCUMENTS

CH    536 354    4/1973

(Continued)

OTHER PUBLICATIONS

STIC Search Report dated on March 5, 2008.*
French Search Report for FR 0551843 (French priority application for the present application), dated Feb. 21, 2006.
English language abstract of EP 0 770 375 B1, May 2, 1997.
English language abstract of JP 2-19576, Jan. 23, 1990.
English language abstract of JP 5-163124, Jun. 29, 1993.
English language Derwent abstract of DE 23 57 448. (Aug. 1975).

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to compositions for the dyeing of human keratin fibers containing at least one compound of the following formula (I):

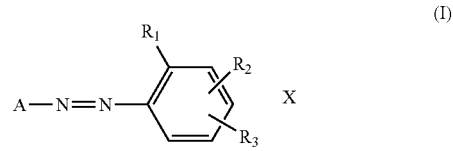

Also disclosed herein is a method for dyeing human keratin fibers comprising applying to the fibers a dyeing composition of the present disclosure until the desired effect is obtained, in the presence or absence of an oxidizing agent, as well as a dyeing compositions containing at least one compound of formula (I).

15 Claims, No Drawings

U.S. PATENT DOCUMENTS

| | | |
|---|---|---|
| 2004/0093676 A1 | 5/2004 | Vidal et al. |
| 2004/0107513 A1 | 6/2004 | Vidal et al. |
| 2004/0127692 A1 | 7/2004 | David et al. |
| 2004/0143911 A1 | 7/2004 | Vidal |
| 2004/0168263 A1 | 9/2004 | Vidal |
| 2004/0187225 A1 | 9/2004 | Vidal et al. |
| 2004/0200009 A1 | 10/2004 | Vidal |
| 2004/0244123 A1 | 12/2004 | Vidal et al. |
| 2005/0039268 A1 | 2/2005 | Plos et al. |
| 2005/0071933 A1 | 4/2005 | Rondeau |
| 2006/0156487 A1 | 7/2006 | Rondeau |

FOREIGN PATENT DOCUMENTS

| | | |
|---|---|---|
| DE | 23 59 399 A1 | 6/1975 |
| DE | 23 57 448 | 8/1975 |
| DE | 25 16 687 | 10/1976 |
| DE | 38 43 892 A1 | 6/1990 |
| DE | 41 33 957 A1 | 4/1993 |
| DE | 195 43 988 A1 | 5/1997 |
| EP | 0 714 954 B1 | 6/1996 |
| EP | 0 770 375 B1 | 5/1997 |
| EP | 1 166 754 A2 | 1/2002 |
| EP | 1 369 105 A1 | 12/2003 |
| FR | 1.199.411 | 12/1959 |
| FR | 1.291.557 | 4/1962 |
| FR | 1.380.628 | 12/1964 |
| FR | 1.462.723 | 2/1966 |
| FR | 1.482.764 | 5/1967 |
| FR | 2.016.982 | 5/1970 |
| FR | 2.080.957 | 11/1971 |
| FR | 2.106.416 | 5/1972 |
| FR | 2.112.050 | 6/1972 |
| FR | 2.202.131 | 5/1974 |
| FR | 2 733 749 A1 | 11/1996 |
| FR | 2 750 048 A1 | 12/1997 |
| FR | 2 757 384 | 6/1998 |
| FR | 2 782 451 A1 | 2/2000 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 A1 | 10/2002 |
| FR | 2 825 625 A1 | 12/2002 |
| FR | 2 825 702 A1 | 12/2002 |
| FR | 2 829 926 A1 | 3/2003 |
| FR | 2 844 269 A1 | 3/2004 |
| GB | 858181 | 1/1961 |
| GB | 860634 | 2/1961 |
| GB | 1 026 978 | 4/1966 |
| GB | 1 153 196 | 5/1969 |
| GB | 1 282 916 | 7/1972 |
| GB | 1 288 718 | 9/1972 |
| GB | 1 313 371 | 4/1973 |
| GB | 1 369 831 | 10/1974 |
| GB | 1 491 930 | 11/1977 |
| GB | 1 508 500 | 4/1978 |
| GB | 1 533 260 | 11/1978 |
| GB | 1 591 532 | 6/1981 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078660 A1 | 10/2002 |
| WO | WO 02/100369 A2 | 12/2002 |
| WO | WO 02/100834 A1 | 12/2002 |
| WO | WO 2005/012437 | 2/2005 |

* cited by examiner

AZO DYES CONTAINING A SULPHONAMIDE OR AMIDE FUNCTION FOR THE DYEING OF HUMAN KERATIN FIBERS AND METHOD OF DYEING AND DYEING COMPOSITIONS CONTAINING THEM

CROSS REFERENCE TO RELATED APPLICATIONS

This application claims benefit of U.S. Provisional Application No. 60/785,986, filed Mar. 27, 2006, the contents of which are incorporated herein by reference. This application also claims benefit of priority under 35 U.S.C. § 119 to French Patent Application No. FR 05 51843, filed Jun. 30, 2005, the contents of which are also incorporated herein by reference.

FIELD OF THE INVENTION

The present disclosure relates to the use of mono- or di-azo dyes containing at least one sulphonamide or amide functional group, for the dyeing of human keratin fibers as well as a method of dyeing.

BACKGROUND OF THE INVENTION

The dyeing of keratin fibers, including human keratin fibers, such as the hair, with dye compositions comprising direct dyes, is known. These compounds are colored and contain coloring molecules having an affinity for the fibers. The use of direct dyes of the nitrobenzene type, anthraquinone dyes, nitropyridines, dyes of the azo, xanthene, acridine, azine or triarylmethane type, for example, is known.

Usually, these dyes are applied to the fibers, optionally in the presence of an oxidizing agent if one wishes to obtain a simultaneous effect of lightening of the fibers. Once the application time has elapsed, the fibers are rinsed, optionally washed and dried.

The dyeing that results from the use of direct dyes is temporary or semi-permanent, as the nature of the interactions which bind the direct dyes to the keratin fiber and their desorption from the surface and/or from the interior of the fiber are responsible for their low dyeing power and for their relatively poor resistance to washing or to sweat.

Some direct dyes may also have inadequate properties of photostability.

Thus, the present disclosure relates to providing direct dyes that do not exhibit the shortcomings of the existing direct dyes.

DETAILED DESCRIPTION OF THE INVENTION

Accordingly, disclosed herein is a cosmetic dyeing composition for dyeing human keratin fibers comprising at least one compound chosen from those of formula (I), and its mesomeric forms thereof:

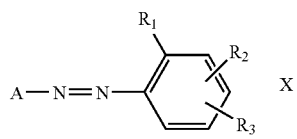

wherein:

A is chosen from monocationic aromatic heterocycles, optionally substituted, containing 5 to 6 ring members, containing at least one nitrogen atom and at least one other heteroatom chosen from nitrogen and sulphur atoms; said heterocycle being optionally condensed with a 6-membered non-heterocyclic aromatic nucleus, optionally substituted; alternatively, A is chosen from optionally-substituted, 6-membered monocationic aromatic heterocycles containing a nitrogen atom, condensed with an optionally-substituted, 6-membered non-heterocyclic aromatic nucleus; and A can be attached to the azo functional group by means of one of the ring members of the heterocycle or of the non-heterocyclic aromatic nucleus;

$R_1$ is chosen from:
—NH—CO—$R'_1$ wherein $R'_1$ is chosen from:
linear and branched $C_1$-$C_6$ alkyl radicals, optionally bearing a trialkyl ($C_1$-$C_4$) ammonium group or optionally bearing a phenoxy group;
amino groups optionally bearing at least one group, which may be identical or different, chosen from $C_1$-$C_4$ alkyl, $C_1$-$C_4$ hydroxyalkyl, and phenyl groups;
—NH—$SO_2$—$R'_2$ wherein $R'_2$ is chosen from linear and branched $C_1$-$C_6$ alkyl radicals;

$R_2$ is chosen from:
hydrogen,
$C_1$-$C_6$ alkoxy groups;
amino groups bearing one or two substituents which may be identical or different, chosen from:
linear and branched $C_1$-$C_6$ alkyl radicals, optionally substituted by at least one group chosen from hydroxyl groups; $C_1$-$C_4$ alkoxy groups; alkoxy($C_1$-$C_4$)carbonyl groups; acyl($C_2$-$C_4$)oxy groups; phenyl groups; and cyano groups;
wherein the two alkyl radicals of said amino group can form, with the nitrogen atom to which they are attached, a 5-membered or 6-membered heterocycle, saturated or unsaturated, optionally containing another heteroatom identical to or different from nitrogen, for example oxygen, or alternatively a sulphur atom bearing two oxygen atoms, and optionally substituted by at least one $C_1$-$C_4$ alkyl radicals;
cyclic $C_5$-$C_7$ alkyl radicals;
naphthyl radicals;
5-membered and 6-membered nitrogen-containing heterocycles, optionally unsaturated, attached to the aromatic nucleus by means of a nitrogen atom, optionally containing another heteroatom chosen from nitrogen or oxygen, said heterocycle being optionally substituted by at least one radical chosen from linear and branched $C_1$-$C_4$ alkyl radicals;
phenyl radicals optionally substituted by at least one group chosen from $C_1$-$C_4$ alkoxy, $C_1$-$C_4$ hydroxyalkoxy, cyano, linear, branched and cyclic $C_1$-$C_6$ alkyl, hydroxyl, amino, amino substituted by one or two $C_1$-$C_4$ alkyl radicals, which may be identical or different, alkyl($C_1$-$C_4$)carbonyl, acetylamino, aminocarbonyl, and carboxy groups, and halogen atoms;
amino groups monosubstituted by a phenyl radical optionally bearing a linear or branched $C_1$-$C_4$ alkoxy group, substituted by a group -D-NH-Φ($R_1$)($R_3$)—N=N-A wherein D is a group chosen from
alkylene($C_1$-$C_2$)—Φ—, —NHCO—Φ—, —O-alkylene ($C_1$-$C_2$)—O—Φ—, and —NH—CO—NH— groupsΦ-, or a single bond; wherein $R_1$, and A are as defined above, and for example, may be chosen in such a way that the radicals $R_1$ and the heterocycles A are respectively identical and occupy the same positions in the molecule; Φ is a phenyl radical;

R₃ is chosen from:

hydrogen;

linear and branched $C_1$-$C_6$ alkyl radicals;

$C_1$-$C_6$ alkoxy groups;

amino groups optionally bearing at least one radical chosen from $C_1$-$C_4$ alkyl, $C_1$-$C_4$ hydroxyalkyl, and phenyl radicals, which may be identical or different;

when $R_2$ and $R_3$ represent two amino groups disubstituted by two alkyl radicals which may be identical or different, carried by two adjacent carbon atoms of the aromatic nucleus, said radicals $R_2$ and $R_3$ can then form, with the carbon atoms to which each is attached, a saturated 6-membered heterocycle optionally substituted by one or two $C_1$-$C_4$ alkyl radicals, linear or branched, which may be identical or different; and one of the carbon atoms of the heterocycle can be replaced by a carbonyl group;

wherein at least one of the two radicals $R_2$ or $R_3$ are different from hydrogen; and X is a cosmetically acceptable anion or mixture of anions.

The present disclosure also relates to a method for dyeing human keratin fibers comprising applying to the fibers a composition comprising at least one compound of formula (I) as defined previously, wherein the fibers may be dry or wet, and the composition is left on the fibers for a sufficient length of time to obtain the desired effect.

The present disclosure also relates to dye compositions comprising, in a medium suitable for the dyeing of human keratin fibers, at least one dye chosen from the compounds of the aforementioned formula (I). In at least one embodiment, the composition further comprises at least one additive chosen from surfactants; anionic, cationic, non-ionic, amphoteric, and zwitterionic polymers; inorganic thickeners; polymeric thickeners; antioxidants; penetrants; sequestering agents; perfumes; buffers; dispersants; conditioners; film-forming agents; ceramides; preservatives; and opacifiers.

It has been found, surprisingly, that the compounds of formula (I) as defined previously have good resistance to external agents, such as shampoos, as well as low selectivity (selectivity meaning the difference in color change between regions of the same hair or between differently sensitized hair).

Further characteristics and benefits of the present disclosure will become clearer on reading the description and examples that will be presented.

In the following, and unless indicated otherwise, the limits of a range of values are included in that range of values.

As used herein, "human keratin fibers" can refer to the hair.

In at least one embodiment of the present disclosure, in formula (I) defined previously, A represents for example, a heterocycle chosen from imidazolium, pyrimidinium, pyrazolium, triazolium, thiazolium, thiadiazolium, quinolinium, benzimidazolium, benzoisothiazolium, and benzothiazolium groups, optionally substituted.

In another embodiment, A is a heterocycle chosen from the thiadiazolium, pyrazolium, thiazolium, benzimidazolium, benzoisothiazolium, benzothiazolium, and triazolium groups, optionally substituted.

In accordance with still another embodiment of the present disclosure, A is chosen from one of the following heterocycles:

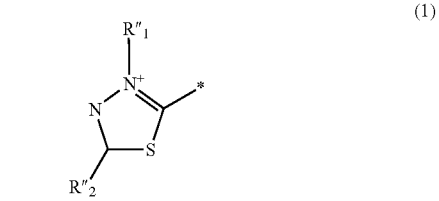

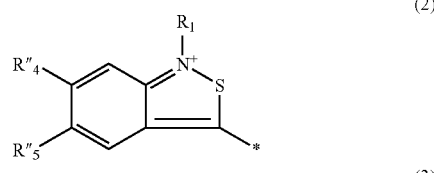

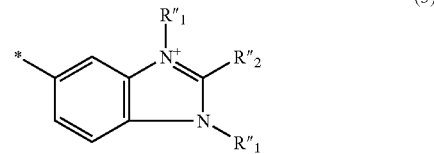

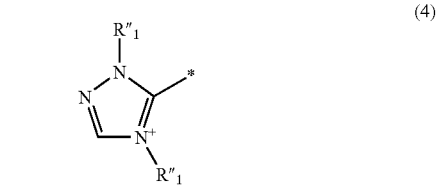

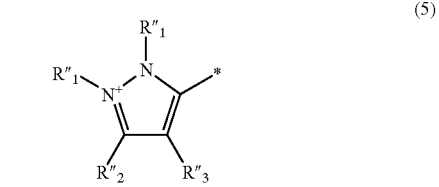

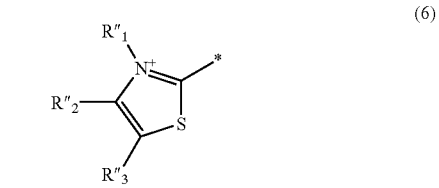

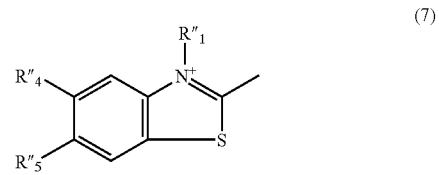

wherein

R"₁ is chosen from:

$C_1$-$C_6$ alkyl radicals optionally substituted by at least one group chosen from hydroxyl groups, cyano groups, aminocarbonyl groups, phenyl groups;

aryl($C_6$)alkyl($C_1$-$C_6$) radicals;

R"₂, R"₃, which may be identical or different, are chosen from:

hydrogen;

linear and branched $C_1$-$C_6$ alkyl groups;

phenyl groups;

amino groups optionally bearing one or two radicals which may be identical or different, chosen from:

linear and branched $C_1$-$C_6$ alkyl radicals optionally substituted by a hydroxyl or cyano group; or $C_5$-$C_7$ cyclic;

phenyl radicals;

tetrahydro-1,1-dioxido-3-thienyl groups;

wherein the two alkyl radicals of the amino group can form, with the nitrogen atom to which they are attached, a 5- to 7-membered heterocycle optionally containing another heteroatom different or not different from nitrogen;

alkoxy($C_1$-$C_6$)carbonyl groups;

$R''_4$, $R''_5$, which may be identical or different, are chosen from:

hydrogen;

linear and branched $C_1$-$C_6$ alkyl groups;

linear and branched $C_1$-$C_6$ alkoxy groups;

halogen atoms, such as chlorine; and nitro groups.

For example, group A can be chosen from thiadiazolium, pyrazolium, thiazolium, benzimidazolium, and triazolium groups, optionally substituted.

According to another embodiment of the disclosure, radical $R_2$ is in the para position relative to the azo functional group.

According to yet another embodiment, radical $R_3$ is in the meta position relative to the azo functional group.

For example, $R_3$ can be chosen from hydrogen and alkoxy radicals, such as methoxy.

According to still another embodiment, $R_2$ can be a substituted amino radical.

For example, $R_1$ can be chosen from acetylamino and methanesulphonamide (or mesylamino) radicals.

In one embodiment, the cosmetically acceptable anion or mixture of anions, X, can be selected from the halides such as chlorides, bromides, fluorides, iodides; hydroxides; sulphates; hydrogensulphates; alkyl($C_1$-$C_6$)sulphates; phosphates; carbonates; hydrogencarbonates; perchlorates; acetates; tartrates; citrates; oxalates; alkyl($C_1$-$C_6$)sulphonates such as methylsulphonate; arylsulphonates which may or may not be substituted by a $C_1$-$C_4$ alkyl radical such as, for example, a 4-toluylsulphonate.

For example, the compound of formula (I) can be selected from the following compounds:

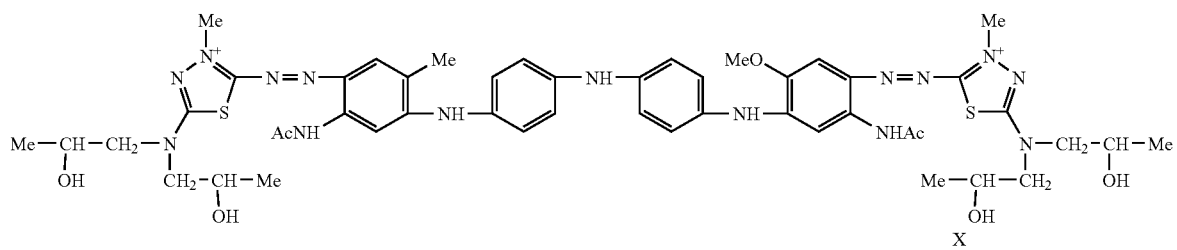

Salt of 1,3,4-Thiadiazolium, 2,2'-[iminobis[4,1-phenylene imino[2-(acetylamino)-5-methoxy-4,1-phenylene]azo]]bis[5-[bis(2-hydroxypropyl)amino]-3-methyl

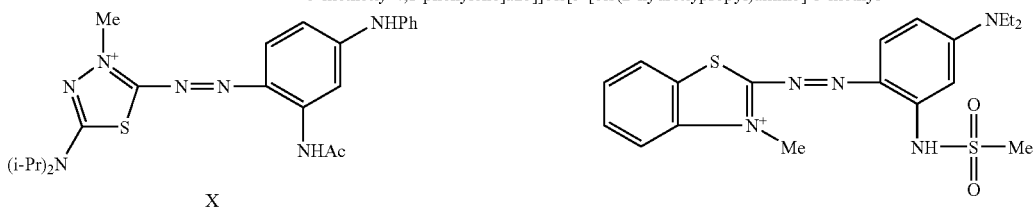

Salt of 1,3,4-Thiadiazolium, 2-[[2-(acetylamino)-4-(phenyl-amino)phenyl]azo]-5-[bis(1-methylethyl)amino]-3-methyl Salt of Benzothiazolium, 2-[[4-(diethylamino)-2-[(methylsulphonyl)amino]phenyl]azo]-3-methyl

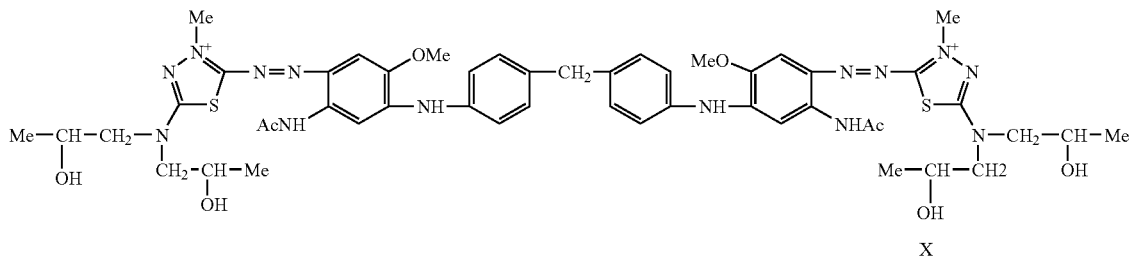

Salt of 1,3,4-Thiadiazolium, 2,2'-[methylenebis[4,1-phenyleneimino[2-(acetylamino)-5-methoxy-4,1-phenylene]azo]]bis[5-[bis(2-hydroxypropyl)amino]-3-methyl -continued

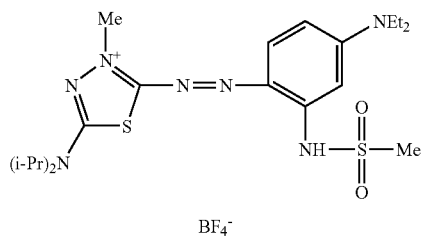

BF$_4^-$

Tetrafluoroborate of 1,3,4-
Thiadiazolium, 5-[bis(1-
methylethyl)amino]-2-[[4-(diethylamino)-
2-[(methylsulphonyl)amino]phenyl]azo]-
3-methyl

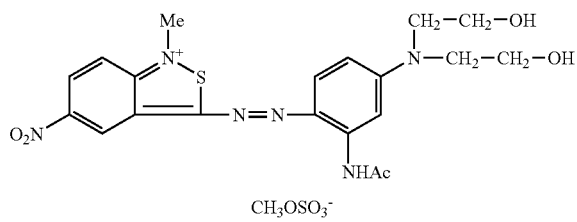

CH$_3$OSO$_3^-$

Methylsulphate of 2,1-
Benzisothiazolium, 3-[[2-
(acetylamino)-4-[bis(2-
hydroxyethyl)amino]phenyl]azo]-1-
methyl-5-nitro

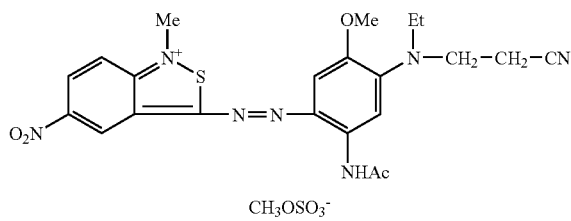

CH$_3$OSO$_3^-$

Methylsulphate of 2,1-
Benzisothiazolium, 3-[[2-(acetylamino)-
4-[(cyanoethyl)ethylamino]-5-
methoxyphenyl]azo]-1-methyl-5-nitro

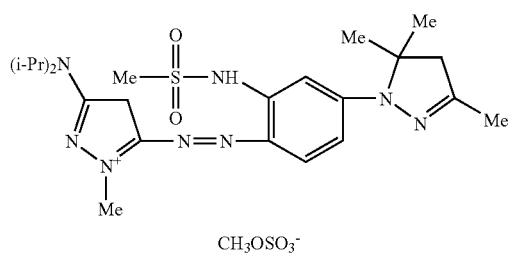

CH$_3$OSO$_3^-$

Methylsulphate of 1,3,4-
Thiadiazolium, 5-[bis(1-
methylethyl)amino]-2-[[4-(4,5-dihydro-
3,5,5-trimethyl-1H-pyrazol-1-yl)-2-
[(methylsulphonyl)amino]phenyl]azo]-3-methyl

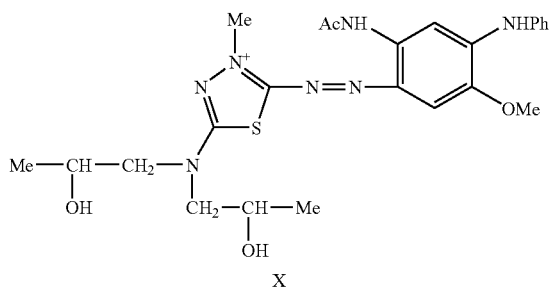

X

Salt of 1,3,4-Thiadiazolium, 2-[[2-
(acetylamino)-5-methoxy-4-
(phenylamino)phenyl]azo]-5-[bis(2-
hydroxypropyl)amino]-3-methyl

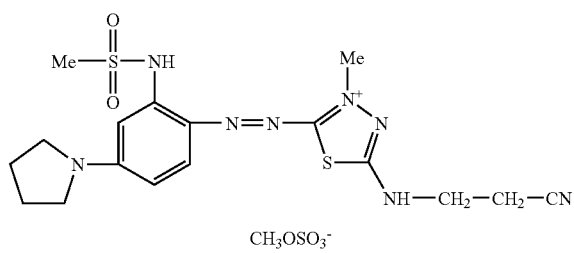

CH$_3$OSO$_3^-$

Methylsulphate of 1,3,4-
Thiadiazolium, 5-[(2-
cyanoethyl)amino]-3-methyl-2-[[2-
[(methylsulphonyl)amino]-4-(1-
pyrrolidinyl)phenyl]azo]

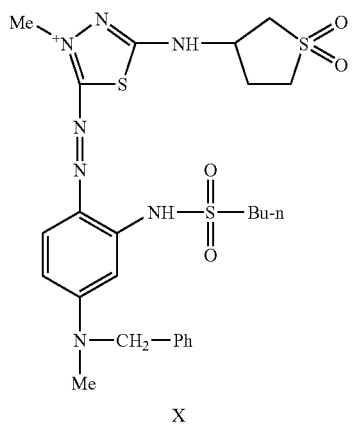

X

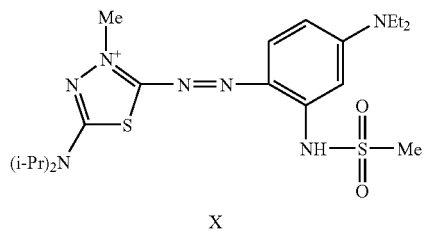

X

-continued

| | |
|---|---|
| Salt of 1,3,4-Thiadiazolium, 2-[[2-[(butylsulphonyl)amino]-4-[methyl(phenylmethyl)amino]phenyl]azo]-3-methyl-5-[(tetrahydro-1,1-dioxido-3-thienyl)amino] | Salt of 1,3,4-Thiadiazolium, 5-[bis(1-methylethyl)amino]-2-[[4-(diethylamino)-2-[(methylsulphonyl)amino]phenyl]azo]-3-methyl |
| 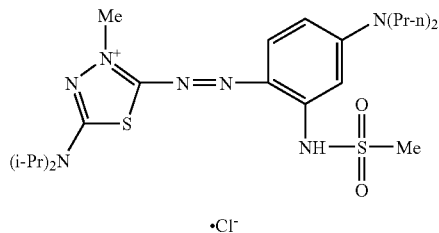 | 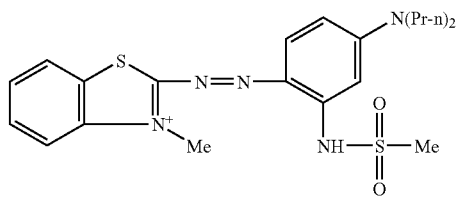 |
| Chloride of 1,3,4-Thiadiazolium, 5-[bis(1-methylethyl)amino]-2-[[4-[(dipropylamino)-2-[(methylsulphonyl)amino]phenyl]azo]-3-methyl | Chloride of Benzothiazolium, 2-[[4-(dipropylamino)-2-[(methylsulphonyl)amino]phenyl]azo]-3-methyl |
| 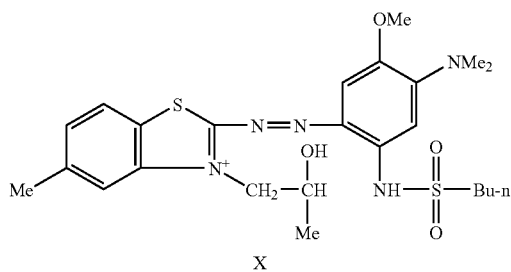 | 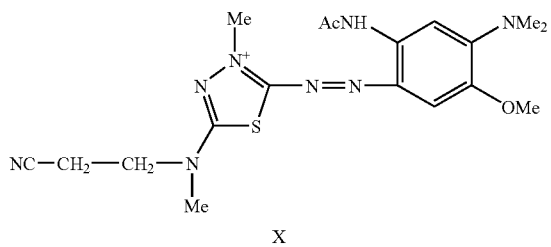 |
| Salt of Benzothiazolium, 2-[[2-[(butylsulphonyl)amino]-4-(dimethylamino)-5-methoxyphenyl]azo]-3-(2-hydroxypropyl)-5-methyl | Salt of 1,3,4-Thiadiazolium, 2-[[2-(acetylamino)-4-(dimethylamino)-5-methylphenyl]azo]-5-[(2-cyanoethyl)methylamino]-3-methyl |
| 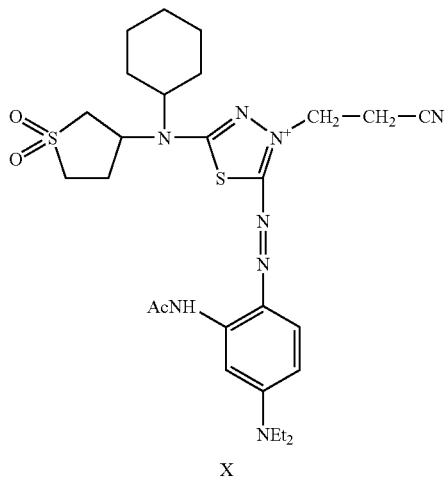 | 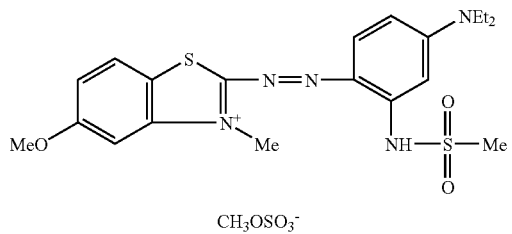 |
| Salt of 1,3,4-Thiadiazolium, 2-[[2-(acetylamino)-4-(diethylamino)phenyl]azo]-3-(2-cyanoethyl)-5-[cyclohexyl(tetrahydro-1,1-dioxido-3-thienyl)amino] | Methylsulphate of Benzothiazolium, 2-[[4-(diethylamino)-2-[(methylsulphonyl)amino]phenyl]azo]-5-methoxy-3-methyl |

-continued

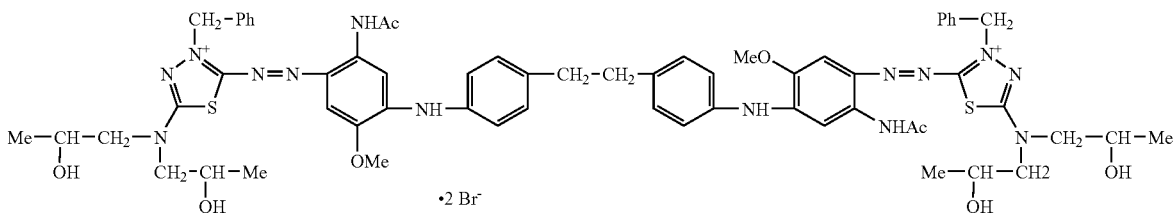

Dibromide of 1,3,4-Thiadiazolium, 2,2'-[1,2-ethanediylbis[4,1-phenyleneimino[2-(acetylamino)-5-methoxy-4,1-phenylene]azo]]bis[5-[bis(2-hydroxypropyl)amino]-3-(phenylmethyl)

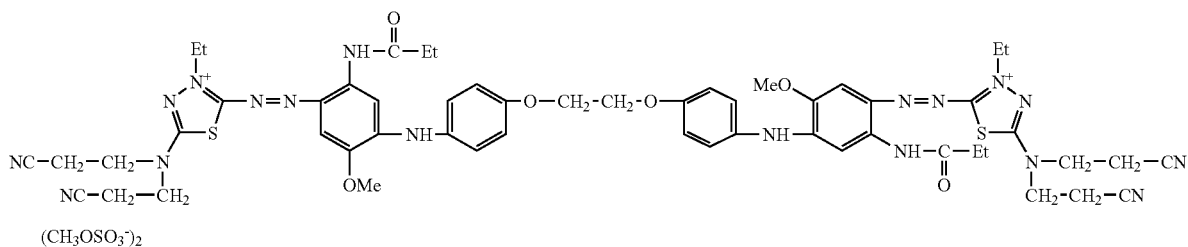

Bis(methylsulphate) of 1,3,4-Thiadiazolium, 2,2'-[1,2-ethanediylbis[oxy-4,1-phenyleneimino[5-methoxy-2-[(1-oxopropyl)amino]-4,1-phenylene]azo]]bis[5-bis(2-cyanoethyl)amino]-3-ethyl

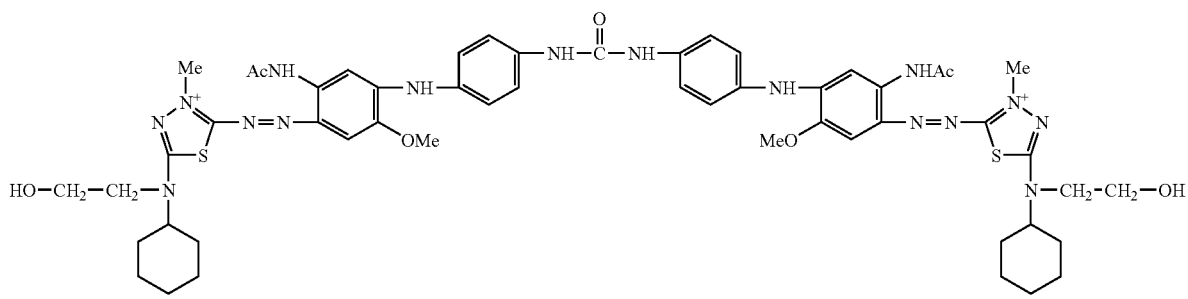

Dichloride of 1,3,4-Thiadiazolium, 2,2'-[carbonylbis[imino-4,1-phenyleneimino[2-(acetylamino)-5-methoxy-4,1-phenylene]azo]]bis[5-[cyclohexyl(2-hydroxyethyl)amino]-3-methyl

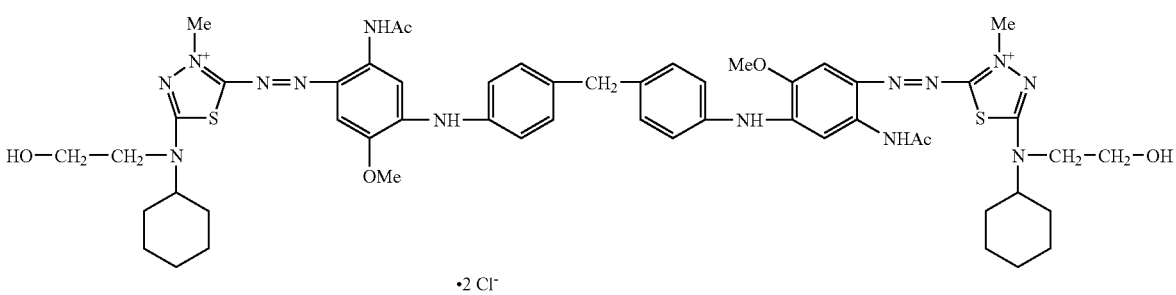

Dichloride of 1,3,4-Thiadiazolium, 2,2'-[methylenebis[4,1-phenyleneimino[2-(acetylamino)-5-methoxy-4,1-phenylene]azo]]bis[5-[cyclohexyl(2-hydroxyethyl)amino]-3-methyl -continued

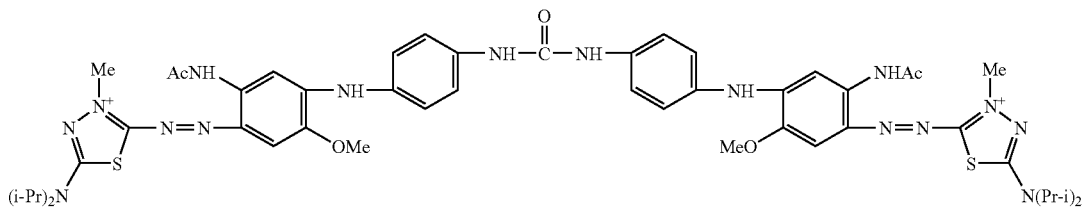

Dichloride of 1,3,4-Thiadiazolium, 2,2'-[carbonylbis[imino-4,1-phenyleneimino[2-(acetylamino)-5-methoxy-4,1-phenylene]azo]]bis[5-[bis(1-methylethyl)amino]-3-methyl

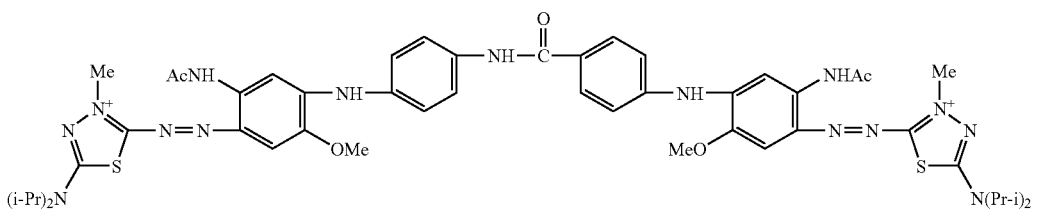

Dichloride of 1,3,4-Thiadiazolium, 2-[[2-(acetyl amino)-4-[[[4-[[5-(acetylamino)-4-[[5-[bis(1-methylethyl)amino]-3-methyl-1,3,4-thiadiazolium-2-yl]azo]-2-methoxyphenyl]amino]phenyl]amino]carbonyl]phenyl]amino]-5-methoxyphenyl]azo]-5-[bis(1-methylethyl)amino]-3-methyl

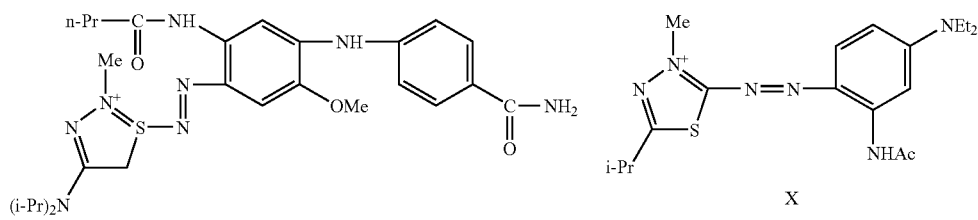

Methylsulphate of 1,3,4-Thiadiazolium, 2-[[4-[[4-(aminocarbonyl)phenyl]amino]-5-methoxy-2-[(1-oxobutyl)amino]phenyl]azo]-5-[bis(1-methylethyl)amino]-3-methyl Salt of 1,3,4-Thiadiazolium, 2-[[2-(acetylamino)-4-(diethylamino)phenyl]azo]-3-methyl-5-(1-methylethyl)

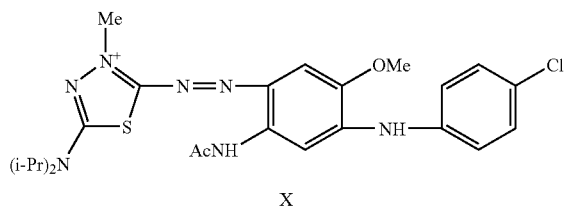

X

Salt of 1,3,4-Thiadiazolium, 2-[[2-(acetylamino)-4-[(4-chlorophenyl)amino]-5-methoxyphenyl]azo]-5-[bis(1-methylethyl)amino]-3-methyl

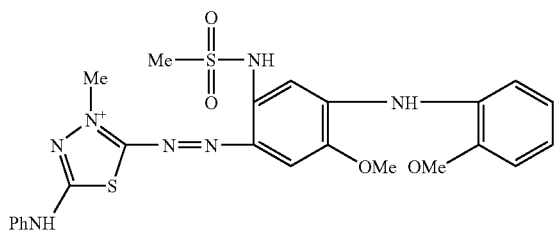

Methylsulphate of 1,3,4-Thiadiazolium, 2-[[5-methoxy-4-[(2-methoxyphenyl)amino]-2-[(methylsulphonyl)amino]phenyl]azo]-3-methyl-5-(phenylamino)

-continued

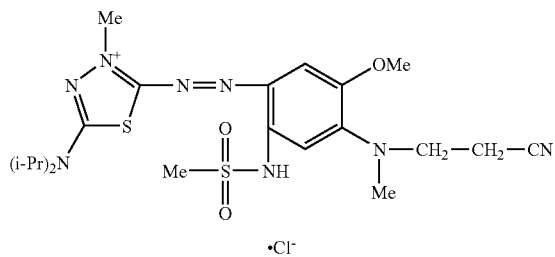

Chloride of 1,3,4-Thiadiazolium, 5-[bis(1-methylethyl)amino]-2-[[4-[(2-cyanoethyl)methylamino]-5-methoxy-2-[(methylsulphonyl)amino]phenyl]azo]-3-methyl

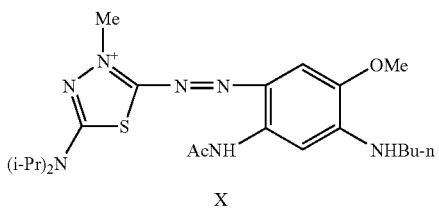

Salt of 1,3,4-Thiadiazolium, 2-[[2-(acetylamino)-4-(butylamino)-5-methoxyphenyl]azo]-5-[bis(1-methylethyl)amino]-3-methyl

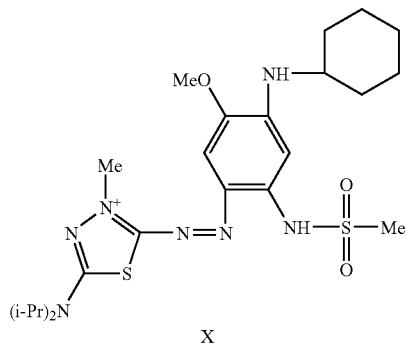

Salt of 1,3,4-Thiadiazolium, 5-[bis(1-methylethyl)amino]-2-[[4-(cyclohexylamino)-5-methoxy-2-[(methylsulphonyl)amino]phenyl]azo]-3-methyl

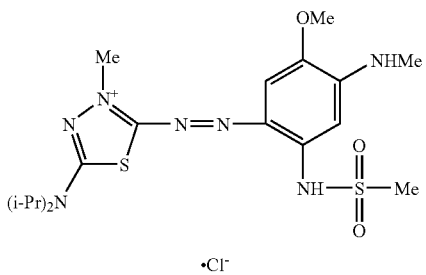

Chloride of 1,3,4-Thiadiazolium, 5-[bis(1-methylethyl)amino]-2-[[5-methoxy-4-(methylamino)-2-[(methylsulphonyl)amino]phenyl]azo]-3-methyl

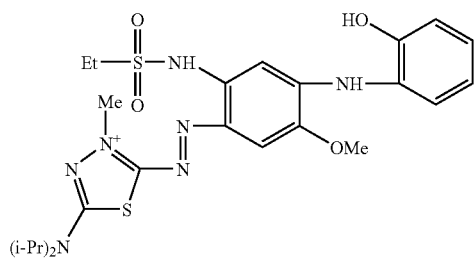

Salt of 1,3,4-Thiadiazolium, 5-[bis(1-methylethyl)amino]-2-[[2-[(ethylsulphonyl)amino]-4-[(2-hydroxyphenyl)amino]-5-methoxyphenyl]azo]-3-methyl

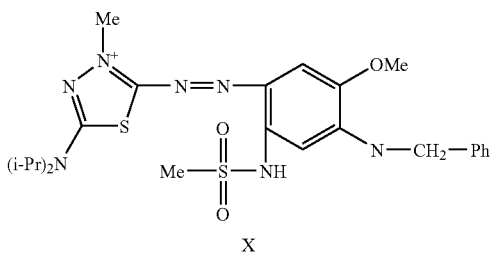

Salt of 1,3,4-Thiadiazolium, 5-[bis(1-methylethyl)amino]-2-[[5-methoxy-2-[(methylsulphonyl)amino]-4-[(phenylmethyl)amino]phenyl]azo]-3-methyl

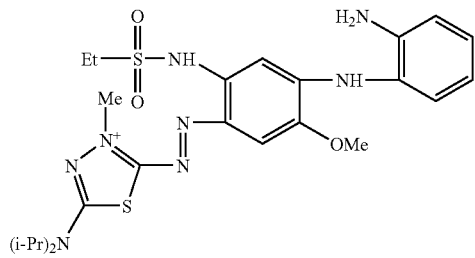

Salt of 1,3,4-Thiadiazolium, 2-[[4-[(2-aminophenyl)amino]-2-[(ethylsulphonyl)amino]-5-

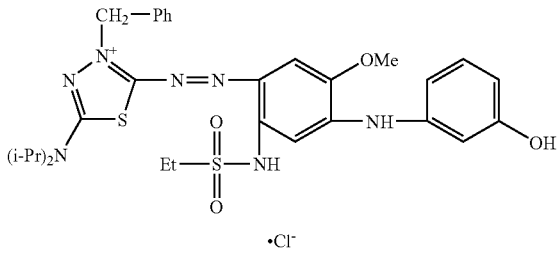

Chloride of 1,3,4-Thiadiazolium, 5-[bis(1-methylethyl)amino]-2-[[2-[(ethylsulphonyl)amino]-4-[(3- methoxyphenyl]azo]-5-[bis(1-methylethyl)amino]-3-methyl

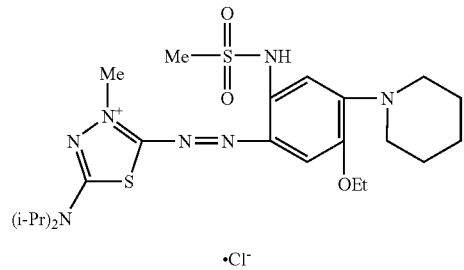

•Cl⁻

Chloride of 1,3,4-Thiadiazolium,5-[bis(1-methylethyl)amino]-2-[[5-ethoxy-2-[(methylsulphonyl)amino]-4-(1-piperidinyl)phenyl]azo]-3-methyl

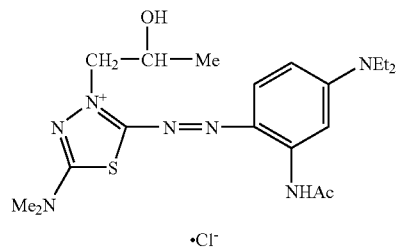

•Cl⁻

Chloride of 1,3,4-Thiadiazolium, 2-[[2-(acetylamino)-4-(diethylamino)phenyl]azo]-5-(dimethylamino)-3-(2-hydroxypropyl)

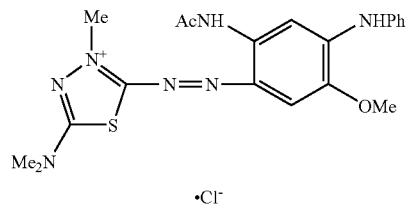

•Cl⁻

Chloride of 1,3,4-Thiadiazolium, 2-[[2-(acetylamino)-5-methoxy-4-(phenylamino)phenyl]azo]-5-(dimethylamino)-3-methyl

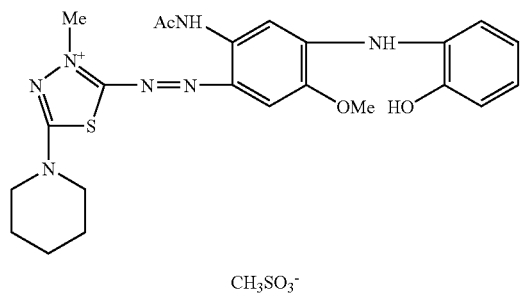

CH₃SO₃⁻

Methylsulphate of
1,3,4-Thiadiazolium, 2-[[2-(acetylamino)-4-[(2- hydroxyphenyl)amino]-5-methoxyphenyl]azo]-3-(phenylmethyl)

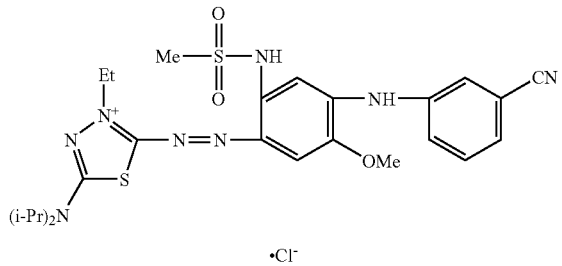

•Cl⁻

Chloride of 1,3,4-Thiadiazolium, 5-[bis(1-methylethyl)amino]-2-[[4-[(3-cyanophenyl)amino]-5-methoxy-2-[(methylsulphonyl)amino]phenyl]azo]-3-ethyl

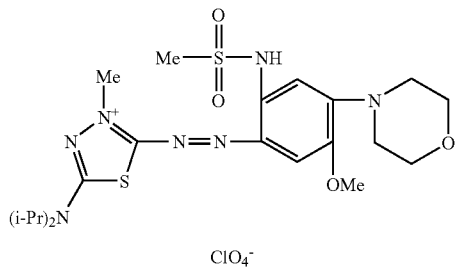

ClO₄⁻

Perchlorate of 1,3,4-Thiadiazolium, 5-[bis(1-methylethyl)amino]-2-[[5-methoxy-2-[(methylsulphonyl)amino]-4-(4-morpholinyl)phenyl]azo]-3-methyl

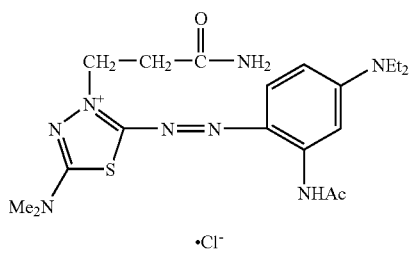

•Cl⁻

Chloride of 1,3,4-Thiadiazolium, 2-[[2-(acetylamino)-4-(diethylamino)phenyl]azo]-3-(3-amino-3-oxopropyl)-5-(dimethylamino)

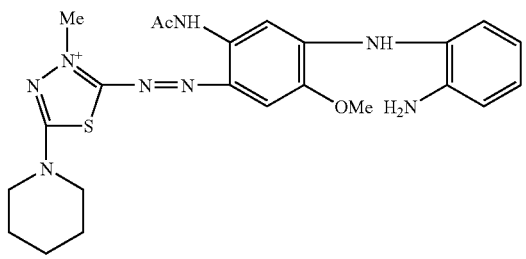

Salt of 1,3,4-Thiadiazolium, 2-[[2-(acetylamino)-4-[(2-aminophenyl)amino]-5- hydroxyphenyl)amino]-5-
methoxyphenyl]azo]-3-methyl-5-(1-
piperidinyl)

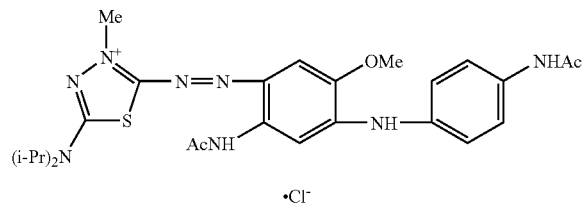

Chloride of 1,3,4-Thiadiazolium, 2-[[2-
(acetylamino)-4-[[4-
(acetylamino)phenyl]amino]-5-
methoxyphenyl]azo]-5-[bis(1-
methylethyl)amino]-3-methyl

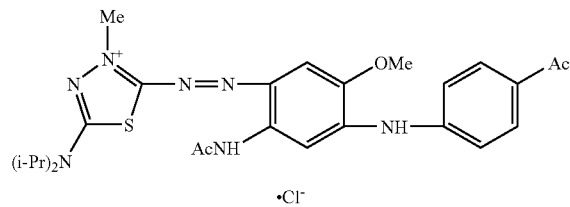

Chloride of 1,3,4-Thiadiazolium, 2-[[2-
(acetylamino)-4-[(4-
acetylphenyl)amino]-5-
methoxyphenyl]azo]-5-[bis(1-
methylethyl)amino]-3-methyl

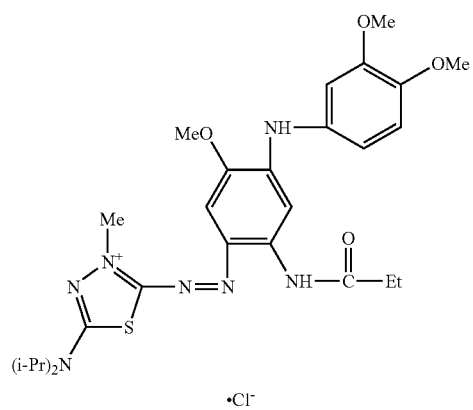

Chloride of 1,3,4-Thiadiazolium, 5-
[bis(1-methylethyl)amino]-2-[[4-[(3,4-
dimethoxyphenyl)amino]-5-methoxy-2-
[(1-oxopropyl)amino]phenyl]azo]-3-
methyl methoxyphenyl]azo]-3-methyl-5-(1-
piperidinyl]

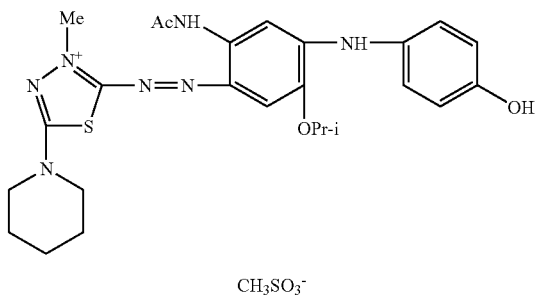

Methylsulphate of 1,3,4-
Thiadiazolium, 2-[[2-(acetylamino)-4-
[(4-hydroxyphenyl)amino]-5-(1-
methylethoxy)phenyl]azo]-3-methyl-5-
(1-piperidinyl)

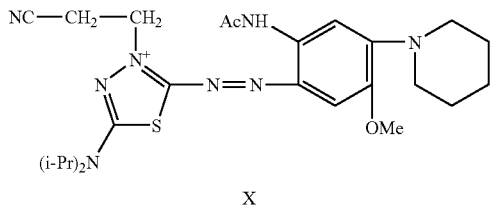

Salt of 1,3,4-Thiadiazolium, 2-[[2-
(acetylamino)-5-methoxy-4-(1-
piperidinyl)phenyl]azo]-5-[bis(1-
methylethyl)amino]-3-(2-cyanoethyl)

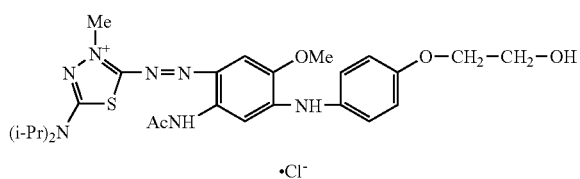

Chloride of 1,3,4-Thiadiazolium, 2-[[2-
(acetylamino)-4-[[4-(2-
hydroxyethoxy)phenyl]amino]-5-
methoxy phenyl]azo]-5-[bis(1-
methylethyl)amino]-3-methyl -continued

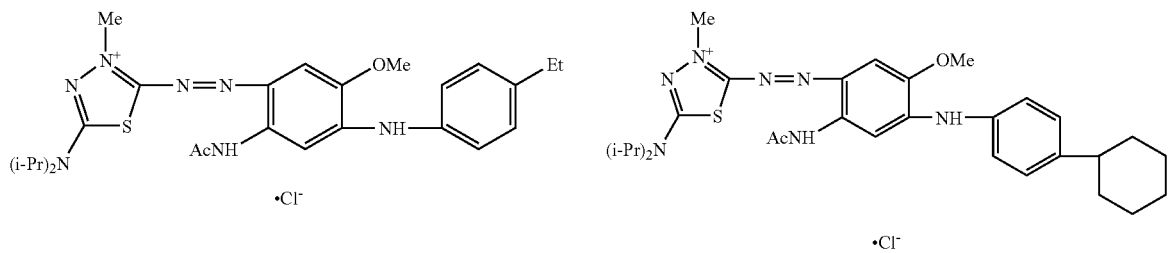

Chloride of 1,3,4-Thiadiazolium, 2-[[2-(acetylamino)-4-[(4-ethylphenyl)amino]-5-methoxyphenyl]azo]-5-[bis(1-methylethyl)amino]-3-methyl Chloride of 1,3,4-Thiadiazolium, 2-[[2-(acetylamino)-4-[(4-cyclohexylphenyl)amino]-5-methoxyphenyl]azo]-5-[bis(1-methylethyl)amino]-3-methyl

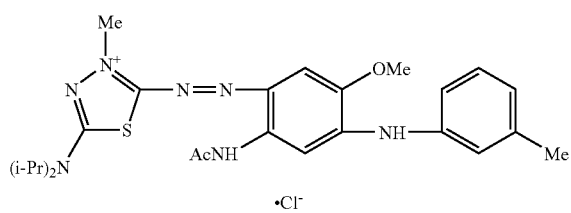

Chloride of 1,3,4-Thiadiazolium, 2-[[2-(acetylamino)-5-methoxy-4-[(3-methylphenyl)amino]phenyl]azo]-5-[bis(1-methylethyl)amino]-3-methyl

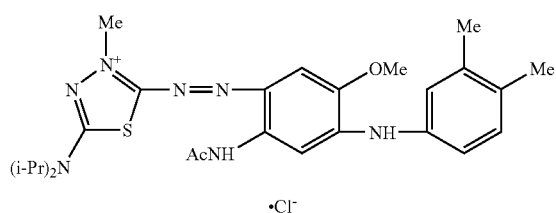

Chloride of 1,3,4-Thiadiazolium, 2-[[2-(acetylamino)-4-[(3,4-dimethylphenyl)amino]-5-methoxyphenyl]azo]-5-[bis(1-methylethyl)amino]-3-methyl

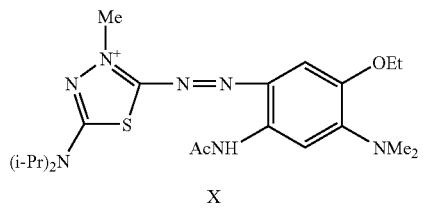

Salt of 1,3,4-Thiadiazolium, 2-[[2-(acetylamino)-4-(dimethylamino)-5-ethoxyphenyl]azo]-5-[bis(1-methylethyl)amino]-3-methyl

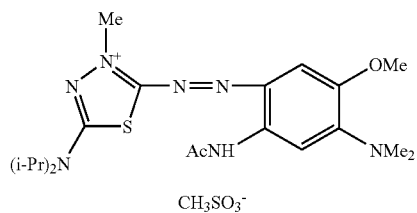

Methylsulphate of 1,3,4-Thiadiazolium, 2-[[2-(acetylamino)-4-(dimethylamino)-5-methylphenyl]azo]-5-[bis(1-methylethyl)amino]-3-methyl

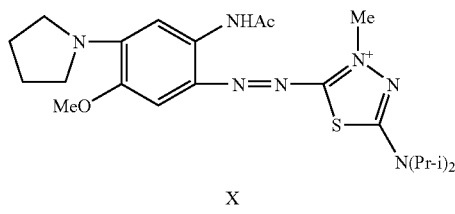

Salt of 1,3,4-Thiadiazolium, 2-[[2-(acetylamino)-5-methoxy-4-(1-pyrrolidinyl)phenyl]azo]-5-[bis(1-methylethyl)amino]-3-methyl

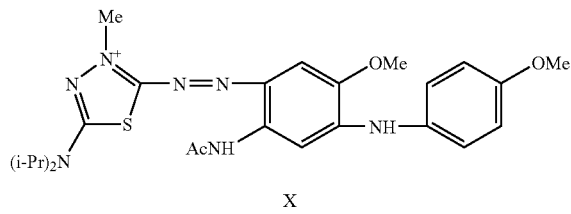

Salt of 1,3,4-Thiadiazolium, 2-[[2-(acetylamino)-5-methoxy-4-[(4-methoxyphenyl)amino]phenyl]azo]-5-[bis(1-methylethyl)amino]-3-methyl

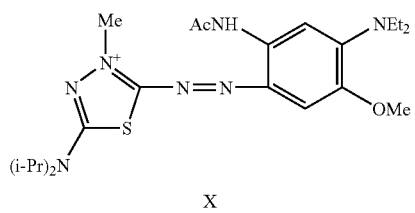

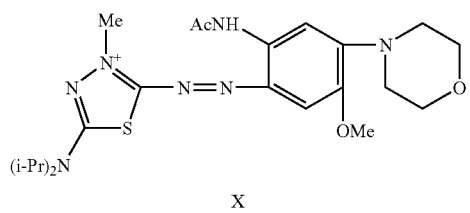

| | |
|---|---|
| Salt of 1,3,4-Thiadiazolium, 2-[[2-(acetylamino)-4-(diethylamino)-5-methoxyphenyl]azo]-5-[bis(1-methylethyl)amino]-3-methyl | Salt of 1,3,4-Thiadiazolium, 2-[[2-(acetylamino)-5-methoxy-4-(4-morpholinyl)phenyl]azo]-5-[bis(1-methylethyl)amino]-3-methyl |
| 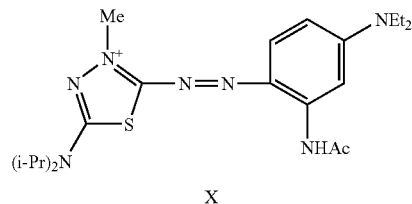<br>X | 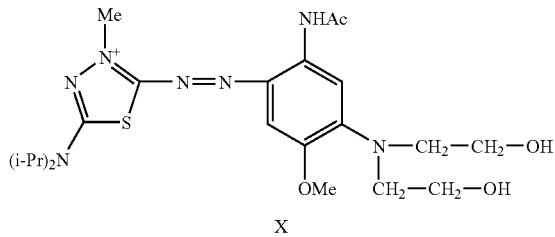<br>X |
| Salt of 1,3,4-Thiadiazolium, 2-[[2-(acetylamino)-4-(diethylamino)phenyl]azo]-5-[bis(1-methylethyl)amino]-3-methyl | Salt of 1,3,4-Thiadiazolium, 2-[[2-(acetylamino)-4-[bis(2-hydroxyethyl)amino]-5-methoxyphenyl]azo]-5-[bis(1-methylethyl)amino]-3-methyl |
| 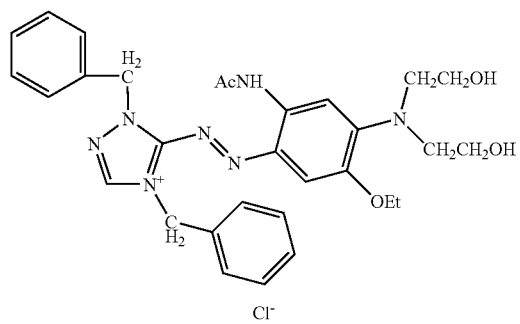<br>Cl⁻ | 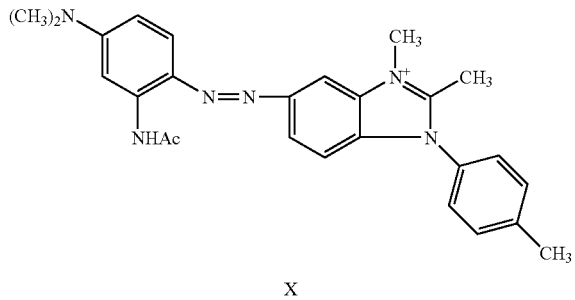<br>X |
| Chloride of 1H-1,2,4-Triazolium, 5-[[2-(acetylamino)-4-[bis(2-hydroxyethyl)amino]-5-ethoxyphenyl]azo]-1,4-bis(phenylmethyl) | Salt of 1H-Benzimidazolium, 5-[[2-(acetylamino)-4-(dimethylamino)phenyl]azo]-2,3-dimethyl-1-(4-methylphenyl) |
| 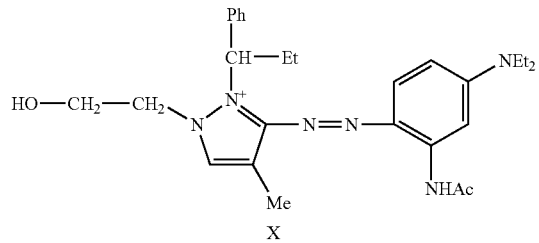<br>X | 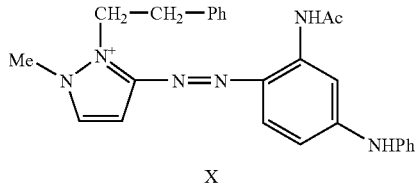<br>X |
| Salt of 1H-Pyrazolium, 3-[[2-(acetylamino)-4-(diethylamino)phenyl]azo]-1-(2-hydroxyethyl)-4-methyl-2-(1-phenylpropyl) | Salt of 1H-Pyrazolium, 3-[[2-(acetylamino)-4-(phenylamino)phenyl]azo]-1-methyl-2-(2-phenylethyl) |
| 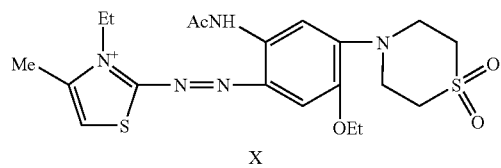<br>X | 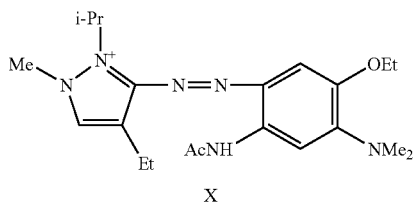<br>X |
| Salt of Thiazolium, 2-[[2-(acetylamino)-4-(1,1-dioxido-4-thiomorpholinyl)-5-ethoxyphenyl]azo]-3-ethyl-4-methyl | Salt of 1H-Pyrazolium, 3-[[2-(acetylamino)-4-(dimethylamino)-5-ethoxyphenyl]azo]-4-ethyl-1-methyl-2-(1-methylethyl) |

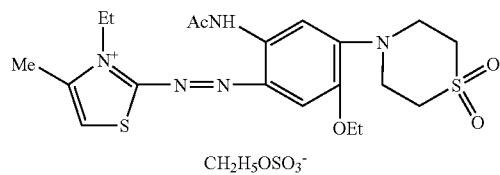

Ethylsulphate of Thiazolium, 2-[(2-acetamido-5-ethoxy-4-thiomorpholinophenyl)azo]-3-ethyl-4-methyl-S,S-dioxide

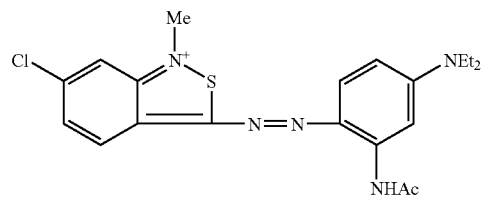

Salt of 2,1-Benzisothiazolium, 3-[[2-(acetylamino)-4-(diethylamino)phenyl]azo]-6-chloro-1-methyl

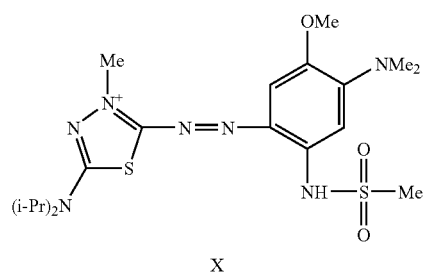

Salt of 1,3,4-Thiadiazolium, 5-[bis(1-methylethyl)amino]-2-[[4-(dimethylamino)-5-methoxy-2-[(methylsulphonyl)amino]phenyl]azo]-3-methyl

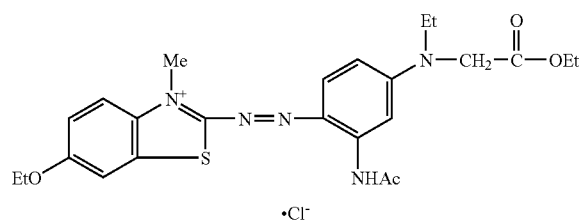

Chloride of Benzothiazolium, 2-[[2-(acetylamino)-4-[(2-ethoxy-2-oxoethyl)ethylamino]phenyl]azo]-6-ethoxy-3-methyl

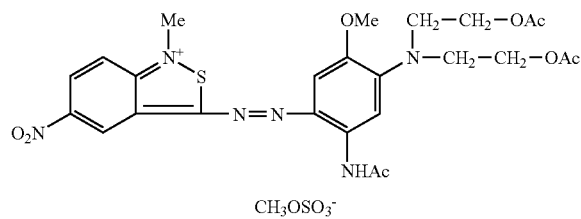

Methylsulphate of 2,1-Benzisothiazolium, 3-[[2-(acetylamino)-4-[bis[2-(acetyloxy)ethyl]amino]-5-methoxyphenyl]azo]-1-methyl-5-nitro

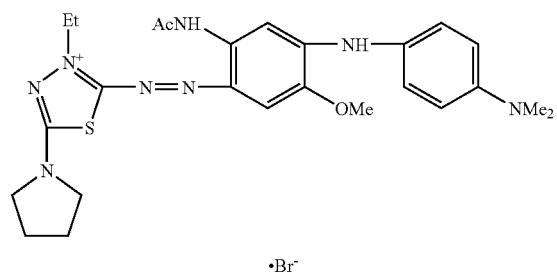

Bromide of 1,3,4-Thiadiazolium, 2-[[2-(acetylamino)-4-[[4-(dimethylamino)phenyl]amino]-5-methoxyphenyl]azo]-3-ethyl-5-(1-pyrrolidinyl)

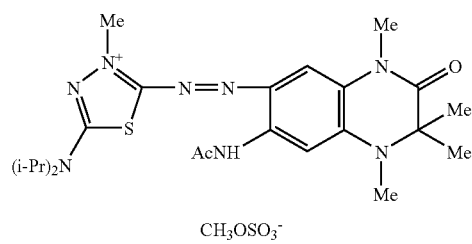

Methylsulphate of 1,3,4-Thiadiazolium, 2-[[7-(acetylamino)-1,2,3,4-tetrahydro-1,2,2,4-tetramethyl-3-oxo-6-quinoxalinyl]azo]-5-[bis(1-methylethyl)amino]-3-methyl

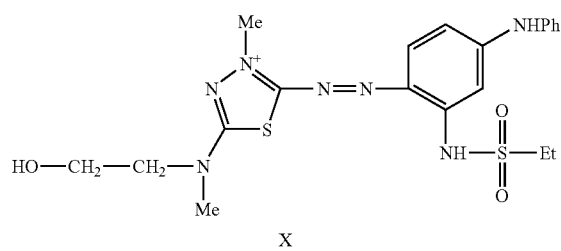

Salt of 1,3,4-Thiadiazolium, 2-[[2-[(ethylsulphonyl)amino]-4-(phenylamino)phenyl]azo]-5-[(2-hydroxyethyl)methylamino]-3-methyl -continued

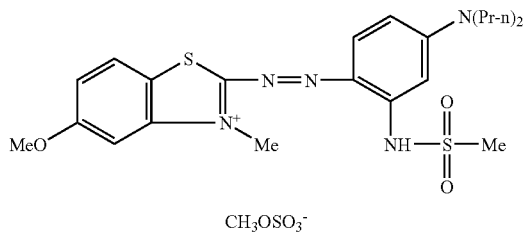

CH₃OSO₃⁻

Methylsulphate of Benzothiazolium, 2-
[[4-(dipropylamino)-2-
[(methylsulphonyl)amino]phenyl]azo]-5-
methoxy-3-methyl

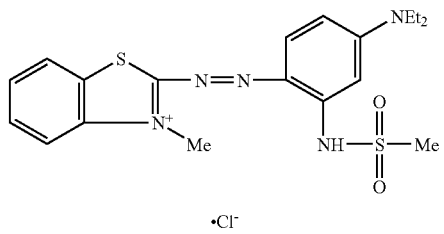

•Cl⁻

Chloride of Benzothiazolium, 2-[[4-
(diethylamino)-2-
[(methylsulphonyl)amino]phenyl]azo]-
3-methyl

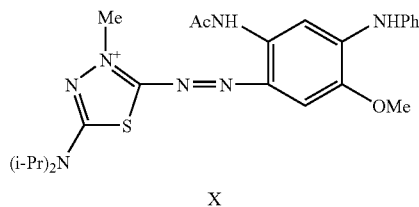

X

Salt of 1,3,4-Thiadiazolium, 2-[[2-
(acetylamino)-5-methoxy-4-
(phenylamino)phenyl]azo]-5-[bis(1-
methylethyl)amino]-3-methyl

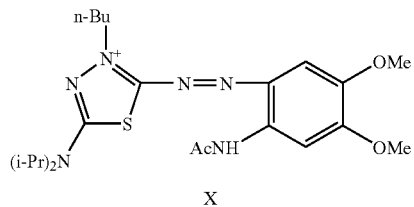

X

Salt of 1,3,4-Thiadiazolium, 2-[[2-
(acetylamino)-4,5-
dimethoxyphenyl]azo]-5-[bis(1-
methylethyl)amino]-3-butyl

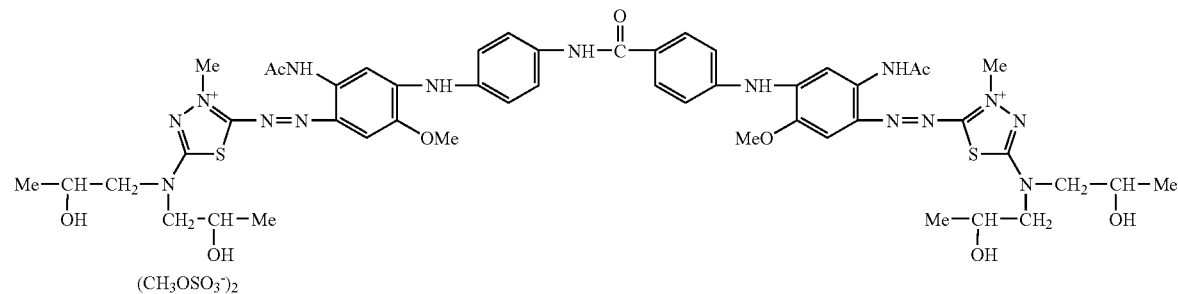

(CH₃OSO₃⁻)₂

Bis(methylsulphate) of 1,3,4-Thiadiazolium, 2-[[2-(acetylamino)-4-[[4-[[[4-[[5-
(acetylamino)-4-[[5-[bis(2-hydroxypropyl)amino]-3-methyl-1,3,4-thiadiazolium
2-yl]azo]-2-methoxyphenyl]amino]phenyl]amino]carbonyl]phenyl]amino]-5-
methoxyphenyl]azo]-5-[bis(2-hydroxypropyl)amino]-3-methyl

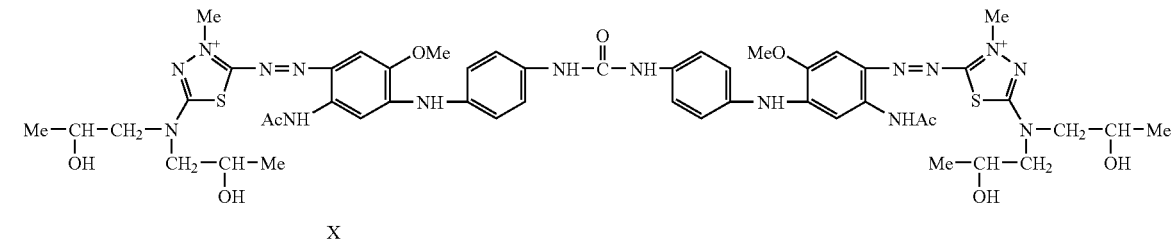

X

Salt of 1,3,4-Thiadiazolium, 2,2'-[carbonylbis[imino-4,1-phenyleneimino[2-
(acetylamino)-5-methoxy-4,1-phenylene]azo]]bis[5-[bis(2-hydroxypropyl)amino]-
3-methyl -continued

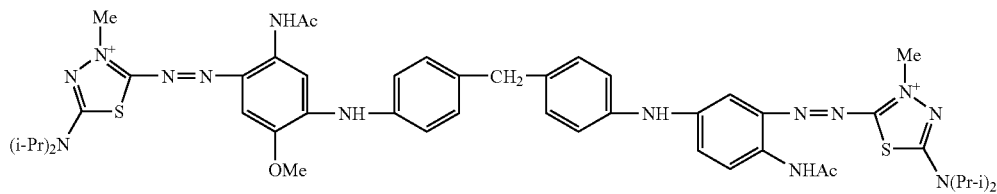

•2 Cl⁻

Dichloride of 1,3,4-Thiadiazolium, 2,2'-[methylenebis[4,1-phenyleneimino[2-(acetylamino)-5-methoxy-4,1-phenylene]azo]]bis[5-[bis(1-methylethyl)amino]-3-methyl

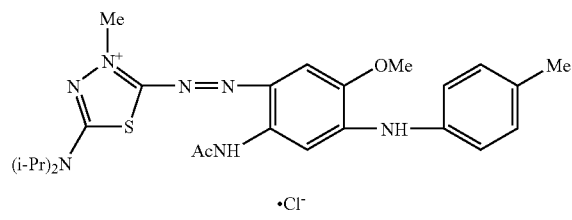

•Cl⁻

Chloride of 1,3,4-Thiadiazolium, 2-[[2-(acetylamino)-5-methoxy-4-[(4-methylphenyl)amino]phenyl]azo]-5-[bis(1-methylethyl)amino]-3-methyl

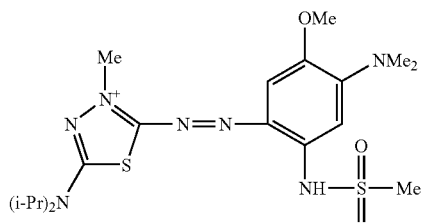

•Cl⁻

Chloride of 1,3,4-Thiadiazolium, 5-[bis(1-methylethyl)amino]-2-[[4-(dimethylamino)-5-methoxy-2-[(methylsulphonyl)amino]phenyl]azo]-3-methyl

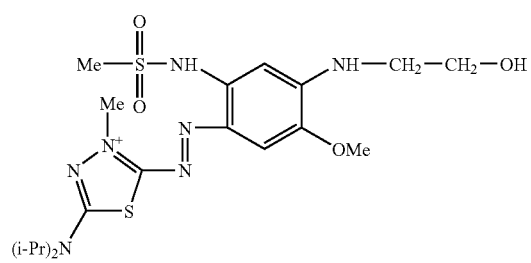

X

Salt of 1,3,4-Thiadiazolium, 5-[bis(1-methylethyl)amino]-2-[[4-[(2-hydroxyethyl)amino]-5-methoxy-2-[(methylsulphonyl)amino]phenyl]azo]-3-methyl

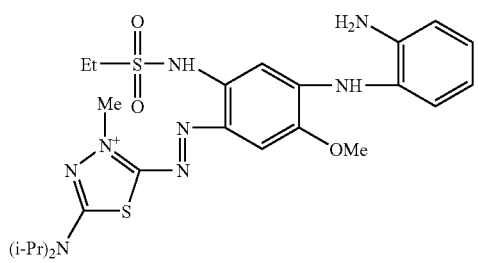

CH₃OSO₃⁻

Methyl sulphate of 1,3,4-Thiadiazolium, 2-[[4-[(2-aminophenyl)amino]-2-[(ethylsulphonyl)amino]-5-methoxyphenyl]azo]-5-[bis(1-methylethyl)amino]-3-methyl

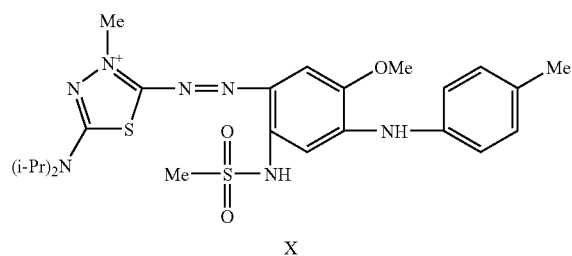

X

Salt of 1,3,4-Thiadiazolium, 5-[bis(1-methylethyl)amino]-2-[[5-methoxy-4-[(4-methylphenyl)amino]-2-[(methylsulphonyl)amino]phenyl]azo]-3-methyl

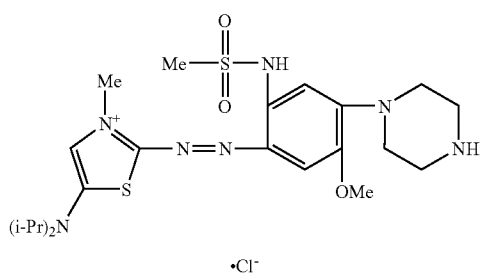

•Cl⁻

Chloride of 1,3,4-Thiadiazolium, 5-[bis(1-methylethyl)amino]-2-[[5-methoxy-2-[(methylsulphonyl)amino]-4-(1-piperazinyl)phenyl]azo]-3-methyl -continued

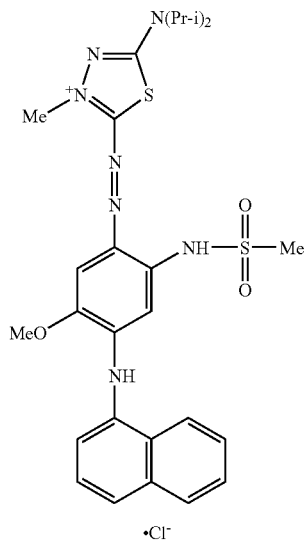

Chloride of 1,3,4-Thiadiazolium, 5-[bis(1-methylethyl)amino]-2-[[5-methoxy-2-[(methylsulphonyl)amino]-4-(1-naphthalenylamino)phenyl]azo]-3-methyl

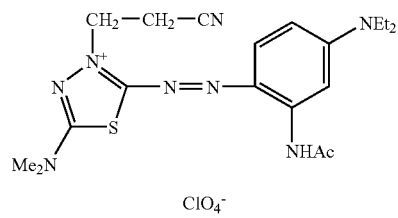

Perchlorate of 1,3,4-Thiadiazolium, 2-[[2-(acetylamino)-4-(diethylamino)phenyl]azo]-3-(2-cyanoethyl)-5-(dimethylamino)

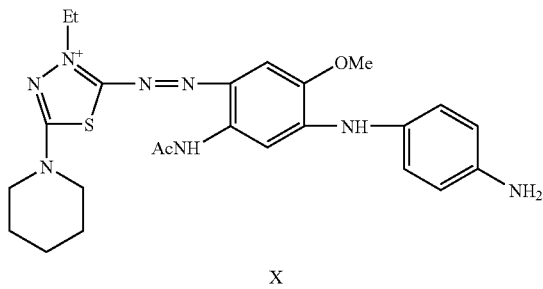

X

Salt of 1,3,4-Thiadiazolium, 2-[[2-(acetylamino)-4-[(4-aminophenyl)amino]-5-methoxyphenyl]azo]-3-ethyl-5-(1-piperidinyl)-ethyl

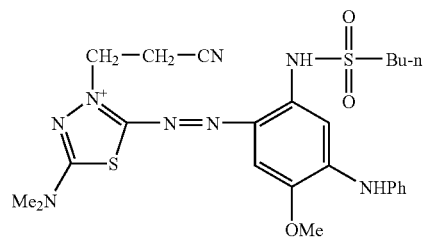

Chloride of 1,3,4-Thiadiazolium, 2-[[2-[(butylsulphonyl)amino]-5-methoxy-4-(phenylamino)phenyl]azo]-3-(2-cyanoethyl)-5-(dimethylamino)

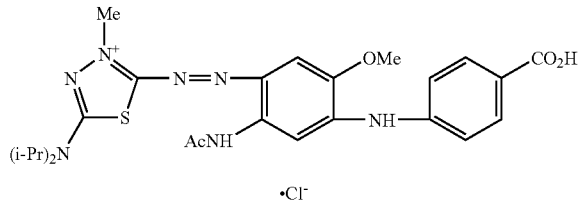

Chloride of 1,3,4-Thiadiazolium, 2-[[2-(acetylamino)-4-[(4-carboxyphenyl)amino]-5-methoxyphenyl]azo]-5-[bis(1-methylethyl)amino]-3-methyl

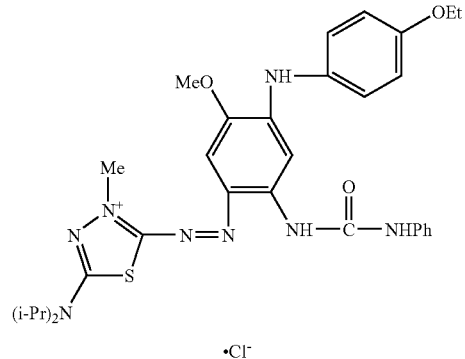

Chloride of 1,3,4-Thiadiazolium, 5-[bis(1-methylethyl)amino]-2-[[4-[(4-ethoxyphenyl)amino]-5-methoxy-2-[[(phenylamino)carbonyl]amino]phenyl]azo]-3-methyl -continued

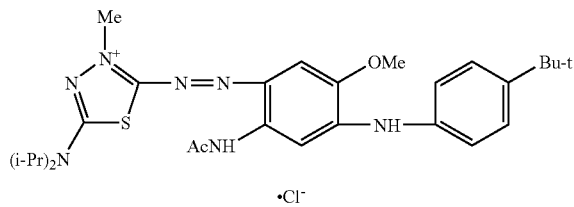

Chloride of 1,3,4-Thiadiazolium, 2-[[2-(acetylamino)-4-[[4-(1,1-dimethylethyl)phenyl]amino]-5-methoxyphenyl]azo]-5-[bis(1-methylethyl)amino]-3-methyl

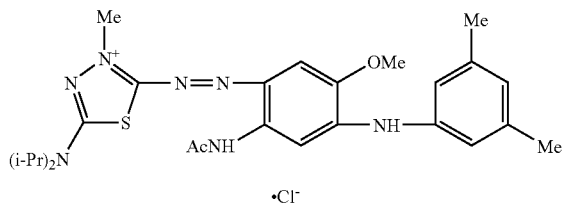

Chloride of 1,3,4-Thiadiazolium, 2-[[2-(acetylamino)-4-[(3,5-dimethylphenyl)amino]-5-methoxyphenyl]azo]-5-[bis(1-methylethyl)amino]-3-methyl

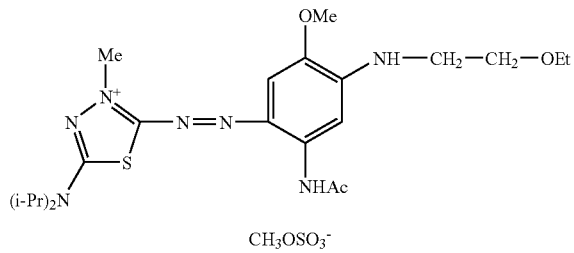

Methyl sulphate of 1,3,4-Thiadiazolium, 2-[[2-(acetylamino)-4-[(2-ethoxyethyl)amino]-5-methoxyphenyl]azo]-5-[bis(1-methylethyl)amino]-3-methyl

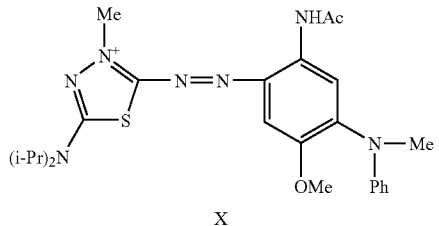

Salt of 1,3,4-Thiadiazolium, 2-[[2-(acetylamino)-5-methoxy-4-(methylphenylamino)phenyl]azo]-5-[bis(1-methylethyl)amino]-3-methyl

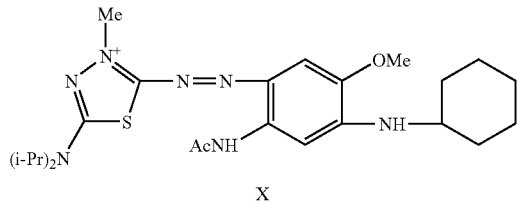

Salt of 1,3,4-Thiadiazolium, 2-[[2-(acetylamino)-4-(cyclohexylamino)-5-methoxyphenyl]azo]-5-[bis(1-methylethyl)amino]-3-methyl

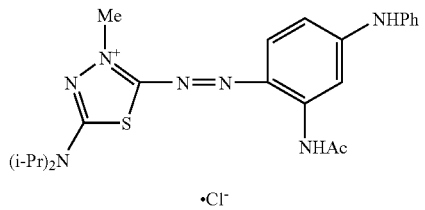

Chloride of 1,3,4-Thiadiazolium, 2-[[2-(acetylamino)-4-(phenylamino)phenyl]azo]-5-[bis(1-methylethyl)amino]-3-methyl

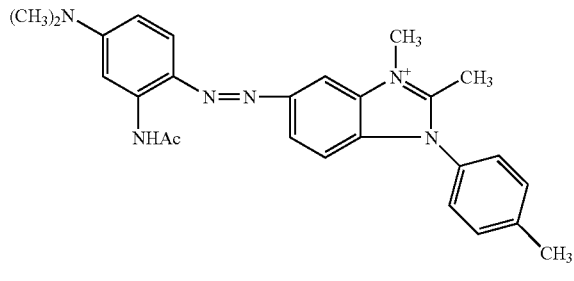

Salt of 1H-Benzimidazolium, 5-[[2-(acetylamino)-4-(dimethylamino)phenyl]azo]-2,3-dimethyl-1-phenyl

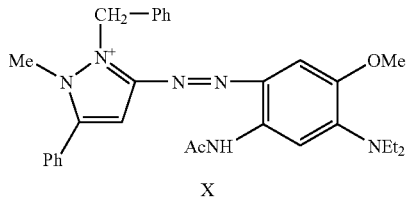

Salt of 1H-Pyrazolium, 3-[[2-(acetylamino)-4-(diethylamino)-5-methoxyphenyl]azo]-1-methyl-5-phenyl-2-(phenylmethyl)

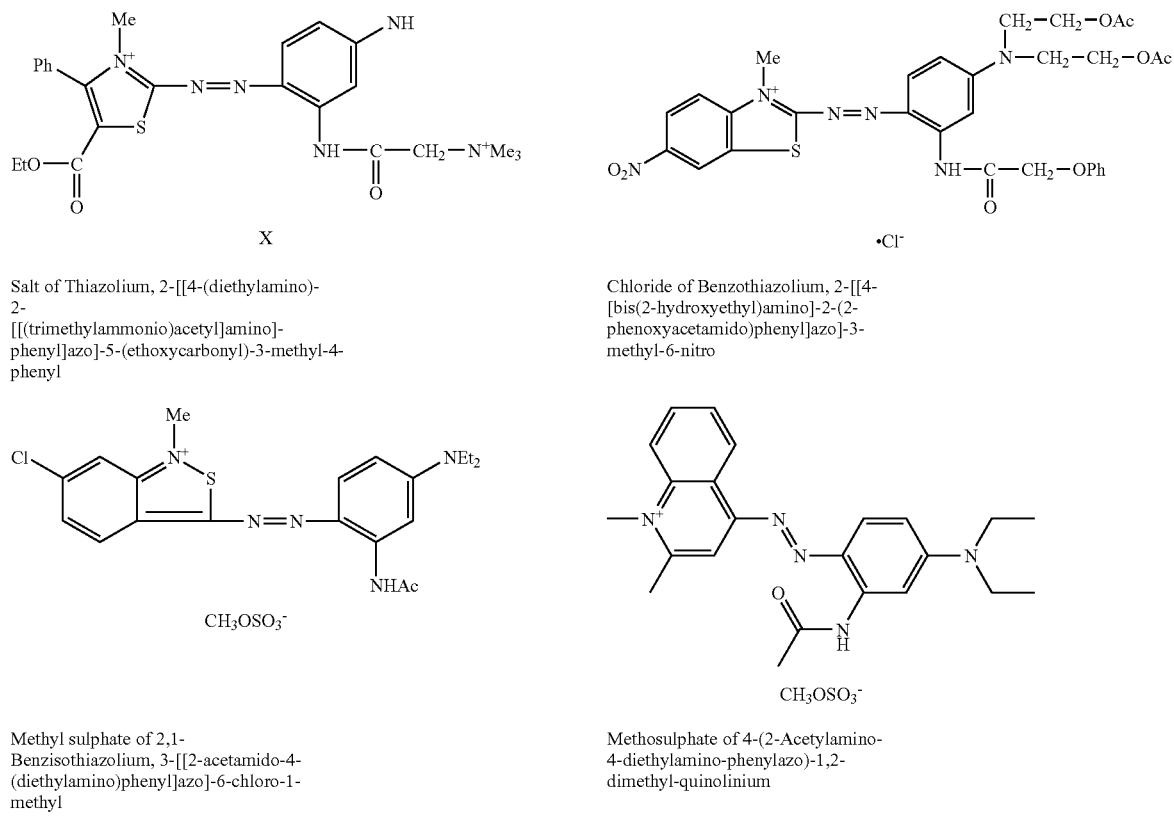

Salt of Thiazolium, 2-[[4-(diethylamino)-2-[[(trimethylammonio)acetyl]amino]-phenyl]azo]-5-(ethoxycarbonyl)-3-methyl-4-phenyl Chloride of Benzothiazolium, 2-[[4-[bis(2-hydroxyethyl)amino]-2-(2-phenoxyacetamido)phenyl]azo]-3-methyl-6-nitro Methyl sulphate of 2,1-Benzisothiazolium, 3-[[2-acetamido-4-(diethylamino)phenyl]azo]-6-chloro-1-methyl Methosulphate of 4-(2-Acetylamino-4-diethylamino-phenylazo)-1,2-dimethyl-quinolinium Note that the nature of the counter-ions shown in the above table is merely given as a guide, and is not limiting.

According to one embodiment of the disclosure, at least one compound of formula (I) can be present in the dyeing composition in an amount ranging from 0.001 wt. % to 10 wt. % relative to the weight of the dyeing composition, such as from 0.05 and 5 wt. % relative to the weight of the dyeing composition.

Another aspect of the present disclosure is a method for dyeing which comprises bringing a dyeing composition containing at least one compound of formula (I) as defined previously, into contact with human keratin fibers, dry or wet.

The dyeing composition employed in the method according to the disclosure can optionally comprise at least one additional direct dye different from the at least one compound of formula (I). It can be chosen from, for example, the cationic or non-ionic species.

Among the cationic or non-ionic species that may be used, mention may be made, as non-limiting examples, of the nitrobenzene dyes, the azo, azomethine, methine, tetraazapenthamethine, anthraquinone, naphthoquinone, benzoquinone, phenothiazine indigo, xanthene, phenanthridine, phthalocyanine dyes, those derived from triarylmethane and the natural dyes, alone or as mixtures.

Among the direct azo dyes that can be used according to the disclosure, non-limiting mention can be made of the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369, FR 2 844 269.

Among the direct natural dyes that can be used according to the disclosure, non-limiting mention may be made of lawsone, juglone, alizarin, purpurin, carminic acid, kermesic acid, purpurogallin, protocatechualdehyde, indigo, isatin, curcumine, spinulosine, and apigenidine. It is also possible to use extracts or decoctions containing these natural dyes, such as henna-based cataplasms or extracts.

If they are present, at least one additional direct dye can be present in the dyeing composition in an amount ranging from 0.001 to 20 wt. % relative to the weight of the composition, such as from 0.01 to 10 wt. % relative to the weight of the composition.

The dyeing composition employed can additionally contain at least one oxidation base.

These oxidation bases can be chosen from the oxidation bases traditionally used in oxidation dyeing, for example the paraphenylenediamines, the bis-phenylalkylenediamines, the para-aminophenols, the ortho-aminophenols and the heterocyclic bases.

Among the paraphenylenediamines, the following examples may be mentioned in a non-limiting manner: paraphenylenediamine, paratoluylenediamine, 2-chloro-paraphenylenediamine, 2,3-dimethyl paraphenylenediamine, 2,6-dimethyl paraphenylenediamine, 2,6-diethyl paraphenylenediamine, 2,5-dimethyl paraphenylenediamine, N,N-dimethyl paraphenylenediamine, N,N-diethyl paraphenylenediamine, N,N-dipropyl paraphenylenediamine, 4-amino N,N-diethyl 3-methyl aniline, N,N-bis-(β-hydroxyethyl) paraphenylenediamine, 4-N,N-bis-(β-hydroxyethyl) amino 2-methyl aniline, 4-N,N-bis-(β-hydroxyethyl)amino 2-chloro aniline, 2-β-hydroxyethyl paraphenylenediamine, 2-fluoro paraphenylenediamine, 2-isopropyl paraphenylenediamine, N-(β-hydroxypropyl) paraphenylenediamine, 2-hydroxymethyl paraphenylenediamine, N,N-dimethyl 3-methyl paraphenylenediamine, N,N-(ethyl, β-hydroxyethyl) paraphenylenediamine, N-(β,γ-dihydroxypropyl) paraphenylenediamine, N-(4'-aminophenyl) paraphenylenediamine, N-phenyl paraphenylenediamine, 2-β-hydroxyethyloxy paraphenylenediamine, 2-β-acetylaminoethyloxy paraphenylenediamine, N-(β-methoxyethyl) paraphenylenediamine, 4-aminophenyl pyrrolidine, 2-thienyl paraphenylenediamine, 2-β hydroxyethylamino 5-aminotoluene and the acid addition salts thereof.

Among the paraphenylenediamines mentioned above, further non-limiting mention may be made of paraphenylenediamine, paratoluylenediamine, 2-isopropyl paraphenylenediamine, 2-β-hydroxyethyl paraphenylenediamine, 2-β-hydroxyethyloxy paraphenylenediamine, 2,6-dimethyl paraphenylenediamine, 2,6-diethyl paraphenylenediamine, 2,3-dimethyl paraphenylenediamine, N,N-bis-(β-hydroxyethyl) paraphenylenediamine, 2-chloro paraphenylenediamine, 2-β-acetylaminoethyloxy paraphenylenediamine, and the acid addition salts thereof.

Among the bis-phenylalkylenediamines, non-limiting mention may be made of, for example, N,N'-bis-(β-hydroxyethyl) N,N'-bis-(4'-aminophenyl) 1,3-diaminopropanol, N,N'-bis-(β-hydroxyethyl) N,N'-bis-(4'-aminophenyl) ethylenediamine, N,N'-bis-(4-aminophenyl) tetramethylenediamine, N,N'-bis-(β-hydroxyethyl) N,N'-bis-(4-aminophenyl) tetramethylenediamine, N,N'-bis-(4-methyl-aminophenyl) tetramethylenediamine, N,N'-bis-(ethyl) N,N'-bis-(4'-amino, 3'-methylphenyl) ethylenediamine, 1,8-bis-(2,5-diamino phenoxy)-3,6-dioxaoctane, and the acid addition salts thereof.

Among the para-aminophenols, non-limiting mention may be made of para-aminophenol, 4-amino 3-methylphenol, 4-amino 3-fluoro phenol, 4-amino 3-hydroxymethylphenol, 4-amino 2-methylphenol, 4-amino 2-hydroxymethylphenol, 4-amino 2-methoxymethylphenol, 4-amino 2-aminomethylphenol, 4-amino 2-(β-hydroxyethyl aminomethyl) phenol, 4-amino 2-fluoro phenol, and the acid addition salts thereof.

Among the ortho-aminophenols, non-limiting mention may be made of 2-aminophenol, 2-amino 5-methylphenol, 2-amino 6-methylphenol, 5-acetamido 2-aminophenol, and the acid addition salts thereof.

Among the heterocyclic bases, non-limiting mention may be made of, pyridine derivatives, pyrimidine derivatives and pyrazole derivatives and derivatives of the pyrazolo[1,2a]pyrazol-1-one type.

Among the pyridine derivatives, non-limiting mention may be made of compounds described for example in patents GB 1 026 978 and GB 1 153 196, such as 2,5-diaminopyridine, 2-(4-methoxyphenyl)amino 3-aminopyridine, 2,3-diamino 6-methoxypyridine, 2-(β-methoxyethyl)amino 3-amino 6-methoxypyridine, 3,4-diaminopyridine, and the acid addition salts thereof.

Among the pyrimidine derivatives, non-limiting mention may be made of compounds described for example in patents DE 2 359 399; JP 88-169 571; JP 05 163 124; EP 0 770 375 or patent application WO 96/15765 such as 2,4,5,6 -tetraaminopyrimidine, 4-hydroxy 2,5,6-triaminopyrimidine, 2-hydroxy 4,5,6-triaminopyrimidine, 2,4-dihydroxy 5,6-diaminopyrimidine, 2,5,6-triaminopyrimidine, and pyrazolopyrimidine derivatives such as those mentioned in patent application FR-A-2 750 048 and among which we may mention pyrazolo-[1,5-a]-pyrimidine-3,7-diamine; 2,5-dimethylpyrazolo-[1,5-a]-pyrimidine-3,7-diamine; pyrazolo-[1,5-a]-pyrimidine-3,5-diamine; 2,7-dimethylpyrazolo-[1,5-a]-pyrimidine-3,5-diamine; 3-amino pyrazolo-[1,5-a]-pyrimidin-7-ol; 3-amino pyrazolo-[1,5-a]-pyrimidin-5-ol; 2-(3-amino pyrazolo-[1,5-a]-pyrimidin-7-ylamino)-ethanol, 2-(7-amino pyrazolo-[1,5-a]-pyrimidin-3-ylamino)-ethanol, 2-[(3-amino-pyrazolo[1,5-a]pyrimidin-7-yl)-(2-hydroxyethyl)-amino]-ethanol, 2-[(7-amino-pyrazolo[1,5-a]pyrimidin-3-yl)-(2-hydroxy-ethyl)-amino]-ethanol, 5,6-dimethylpyrazolo-[1,5-a]-pyrimidine-3,7-diamine, 2,6-dimethylpyrazolo-[1,5-a]-pyrimidine-3,7-diamine, 2,5, N 7, N 7-tetramethylpyrazolo-[1,5-a]-pyrimidine-3,7-diamine, 3-amino-5-methyl-7-imidazolylpropylamino pyrazolo-[1,5-a]-pyrimidine and the acid addition salts thereof, and their tautomeric forms, when a tautomeric equilibrium exists.

Among the pyrazole derivatives, non-limiting mention may be made of compounds described in patents DE 3 843 892, DE 4 133 957 and patent applications WO 94/08969, WO 94/08970, FR-A-2 733 749 and DE 195 43 988 such as 4,5-diamino 1-methylpyrazole, 4,5-diamino 1-(β-hydroxyethyl) pyrazole, 3,4-diamino pyrazole, 4,5-diamino 1-(4'-chlorobenzyl) pyrazole, 4,5-diamino 1,3-dimethylpyrazole, 4,5-diamino 3-methyl 1-phenyl pyrazole, 4,5-diamino 1-methyl 3-phenyl pyrazole, 4-amino 1,3-dimethyl 5-hydrazino pyrazole, 1-benzyl 4,5-diamino 3-methylpyrazole, 4,5-diamino 3-tert-butyl 1-methyl pyrazole, 4,5-diamino 1-tert-butyl 3-methylpyrazole, 4,5-diamino 1-(β-hydroxyethyl) 3-methylpyrazole, 4,5-diamino 1-ethyl 3-methylpyrazole, 4,5-diamino 1-ethyl 3-(4'-methoxyphenyl) pyrazole, 4,5-diamino 1-ethyl 3-hydroxymethylpyrazole, 4,5-diamino 3-hydroxymethyl 1-methylpyrazole, 4, 5-diamino 3-hydroxymethyl 1-isopropyl pyrazole, 4,5-diamino 3-methyl 1-isopropyl pyrazole, 4-amino 5-(2'-aminoethyl)amino 1,3-dimethyl pyrazole, 3,4,5-triamino pyrazole, 1-methyl 3,4,5-triamino pyrazole, 3,5-diamino 1-methyl 4-methylamino pyrazole, 3,5-diamino 4-(β-hydroxyethyl)amino 1-methylpyrazole, and the acid addition salts thereof.

Among the derivatives of type pyrazolo[1,2a]pyrazol-1-one, non-limiting mention may be made of compounds such as 2,3-diamino-6,7-dihydro,1H-5H-pyrazolo[1,2a]pyrazol-1-one.

The at least one oxidation base can be present in an amount ranging from 0.001 to 10 wt. % relative to the weight of the dyeing composition, such as from 0.005 to 6 wt. % relative to the weight of the dyeing composition.

The dyeing composition employed can also comprise at least one coupling agent conventionally used for the dyeing of human keratin fibers.

Among these coupling agents, non-limiting mention may be made of metaphenylenediamines, meta-aminophenols, metadiphenols, naphthalenic coupling agents and heterocyclic coupling agents.

As non-limiting examples, we may mention 2-methyl 5-aminophenol, 5-N-(β-hydroxyethyl)amino 2-methylphenol, 6-chloro-2-methyl-5-aminophenol, 3-aminophenol, 1,3-dihydroxy benzene, 1,3-dihydroxy 2-methyl benzene, 4-chloro 1,3-dihydroxy benzene, 2,4-diamino 1-(β-hydroxyethyloxy) benzene, 2-amino 4-(β-hydroxyethylamino) 1-methoxybenzene, 1,3-diamino benzene, 1,3-bis-(2,4-diaminophenoxy) propane, 3-ureido aniline, 3-ureido 1-dimethylamino benzene, sesamol, 1-β-hydroxyethylamino-3,4-methylenedioxybenzene, α-naphthol, 2 methyl-1-naphthol, 6-hydroxy indole, 4-hydroxy indole, 4-hydroxy N-methyl indole, 2-amino-3-hydroxy pyridine, 6-hydroxy benzomorpholine, 3,5-diamino-2,6-dimethoxypyridine, 1-N-(β-hydroxyethyl)amino-3,4-methylene dioxybenzene, 2,6-bis-(β-hydroxyethylamino)toluene and the acid addition salts thereof.

In the disclosed composition, the at least one coupling agent, if present, can be present in an amount ranging from 0.001 and 10 wt. % relative to the weight of the dyeing composition, for instance, from 0.005 to 6 wt. % relative to the weight of the dyeing composition.

In one embodiment, the acid addition salts that can be used for oxidation bases and coupling agents can be chosen from, for example, hydrochlorides, hydrobromides, sulphates, citrates, succinates, tartrates, lactates, tosylates, benzenesulphonates, phosphates and acetates.

The dyeing composition employed contains a suitable medium for dyeing, also called dyeing support. The medium can comprise water, or a mixture of water and at least one organic solvent for solubilizing compounds that would not be sufficiently water-soluble.

For example, the organic solvents can be chosen from monoalcohols and diols, linear and branched, and optionally saturated, containing from 2 to 10 carbon atoms, such as ethanol, isopropyl alcohol, hexyleneglycol (2-methyl 2,4-pentanediol), neopentylglycol and 3-methyl-1,5-pentanediol; aromatic alcohols such as benzyl alcohol, phenylethyl alcohol; glycols or glycol ethers such as, for example, monomethyl, monoethyl and monobutyl ethers of ethyleneglycol, propyleneglycol and its ethers such as, for example, monomethylether of propyleneglycol, butyleneglycol, dipropyleneglycol; as well as alkylethers of diethyleneglycol, such as $C_1$-$C_4$, for example, monoethylether and monobutylether of diethyleneglycol, alone or mixed together.

The at least one solvent described above, if present, can be present in an amount ranging from 1 to 40 wt. %, such as from 5 to 30 wt. %, relative to the total weight of the dyeing composition.

The dyeing composition can also comprise at least one additive traditionally used in compositions for dyeing the hair, such as surfactants such as anionic, cationic, non-ionic, amphoteric, zwitterionic surfactants or mixtures thereof; anionic, cationic, non-ionic, amphoteric, zwitterionic polymers or mixtures thereof; inorganic thickeners; polymeric thickeners, and in particular anionic, cationic, non-ionic and amphoteric associative polymeric thickeners; antioxidants; penetrants; sequestering agents; perfumes; buffers; dispersants; conditioners such as for example volatile or non-volatile silicones, modified or unmodified; film-forming agents; ceramides; preservatives; and opacifiers, etc.

The at least one additive, when present, can be present in an amount, for each additive, ranging from 0.01 to 20 wt. % relative to the weight of the dyeing composition.

The pH of the dyeing composition can range from 3 to 12, such as from 5 to 11. It can be adjusted to the desired value by means of acidifying or alkalizing agents usually used in the dyeing of keratin fibers or alternatively by means of conventional buffering systems.

Among acidifying agents, non-limiting mention may be made, as examples, of organic or inorganic acids such as hydrochloric acid, orthophosphoric acid, sulphuric acid, carboxylic acids such as acetic acid, tartaric acid, citric acid, lactic acid, sulphonic acids.

Among alkalizing agents, non-limiting mention may be made, as examples, of ammonia, alkali carbonates, alkanolamines such as mono-, di- and triethanolamines as well as their derivatives, hydroxides of sodium or of potassium and compounds of the following formula:

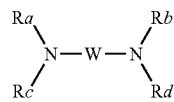

in which W is a propylene residue optionally substituted by a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl or $C_1$-$C_4$ hydroxyalkyl radical.

The dyeing composition according to the disclosure can be in various forms, such as in the form of liquids, creams or gels, or in any other form suitable for carrying out the dyeing of human keratin fibers.

The composition employed in the method according to the disclosure can additionally comprise at least one oxidizing agent. It is then called a ready-to-use composition.

By ready-to-use composition, in the sense of the present disclosure, it is understood to mean a composition intended to be applied immediately to keratin fibers, i.e. that it can be stored as it is before use or results from the mixing of two or more compositions at the time of use.

Usually, the ready-to-use composition is obtained by mixing the oxidant-free dyeing composition with an oxidizing composition.

It should be noted that the simultaneous or successive application of a composition containing at least one compound of formula (I), not containing an oxidizing agent, and a composition containing at least one oxidizing agent, would not be excluded from the definition of ready-to-use composition.

The oxidizing agent can be any agent of this type used traditionally in this area. Thus, the at least one oxidizing agent can be chosen from hydrogen peroxide, urea peroxide, bromates of alkali metals, per-salts such as perborates and persulphates, as well as enzymes, such as peroxidases, oxidoreductases with 2 electrons such as uricases and oxygenases with 4 electrons such as laccases. In one embodiment, hydrogen peroxide is used.

The at least on oxidizing agent can be present in an amount ranging from 1 and 40 wt. %, relative to the weight of the ready-to-use composition, for instance from 1 and 20 wt. % relative to the weight of the ready-to-use composition.

The oxidizing composition can also contain at least one additive traditionally used in compositions for the dyeing of human keratin fibers and as defined previously.

Generally, the oxidizing composition used is an aqueous composition and can be in the form of a solution or of an emulsion.

The oxidant-free dyeing composition can be mixed with about 0.5 to 10 equivalents by weight of the oxidizing composition.

Note that the pH of the ready-to-use composition ranges, for example, from 4 to 12, such as from 7 to 11.5.

The pH of the ready-to-use composition can also be adjusted by means of an alkalizing or acidifying agent, such as those mentioned previously.

The composition which is finally applied to the keratin fibers can be in various forms, such as in the form of liquids, creams, gels or in any other form suitable for the dyeing of human keratin fibers.

According to one embodiment, the composition according to the disclosure does not contain an oxidation base or coupling agent.

The composition that is brought into contact with human keratin fibers can optionally contain at least one oxidizing agent.

Accordingly, the composition is applied to the keratin fibers, dry or wet, then left for a holding time sufficient to obtain the required coloring.

Regardless of the variant adopted (with or without oxidizing agent) the period of coloration time can range from several seconds to 30 minutes, for instance from 3 to 15 minutes.

The temperature at which the composition is left to act can range from 15 to 220° C., for instance from 15 to 80° C., and from 15 to 40° C.

At the end of the coloration time, the composition is removed by rinsing with water, followed by washing with shampoo, then optionally drying.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

The following three compositions were prepared:

| Compound | Quantity (g) |
|---|---|
| Dye (*) | 0.25 g |
| Decylglucoside | 8 g AS (**) |
| pH regulator | qsf pH 8.0 |
| Water | qsf 100 g |

(**) Expressed in g of active substance
(*) Dye definitions

Composition 1-containing dye 1 of the following formula:

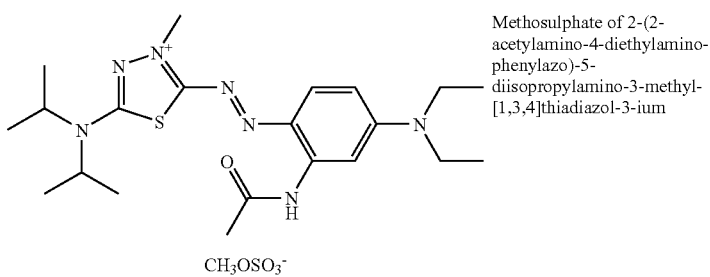

Methosulphate of 2-(2-acetylamino-4-diethylamino-phenylazo)-5-diisopropylamino-3-methyl-[1,3,4]thiadiazol-3-ium Composition 2-containing dye 2 of the following formula:

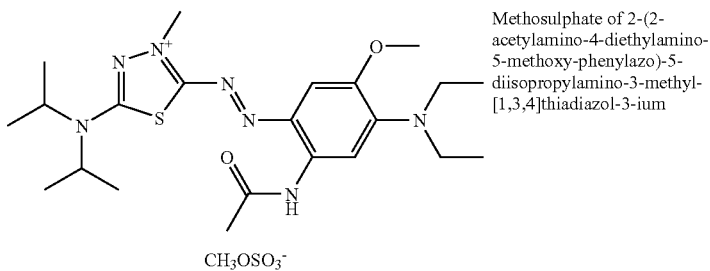

Methosulphate of 2-(2-acetylamino-4-diethylamino-5-methoxy-phenylazo)-5-diisopropylamino-3-methyl-[1,3,4]thiadiazol-3-ium -continued Composition 3-containing dye 3 of the following formula:

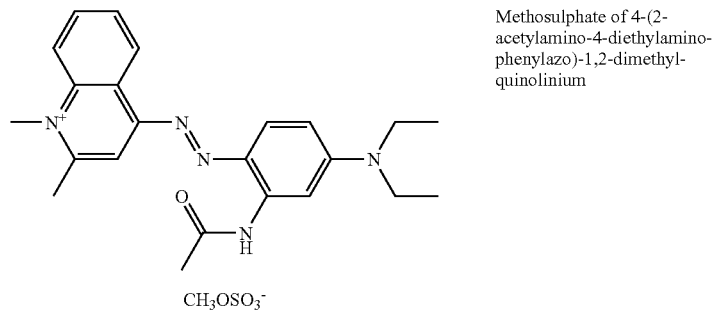

Methosulphate of 4-(2-acetylamino-4-diethylamino-phenylazo)-1,2-dimethyl-quinolinium Each of the three compositions was applied to locks of natural hair with 90% white, at room temperature for 30 minutes.

After 30 minutes, each lock was rinsed and washed with shampoo, rinsed again and then dried.

The following colors were obtained:

Dye 1 reddish blue

Dye 2 blue

Dye 3 blue.

What is claimed is:

1. A cosmetic composition for dyeing human keratin fibers, comprising, in a cosmetically acceptable medium, at least one dye chosen from compounds of formula (I), and mesomeric forms thereof:

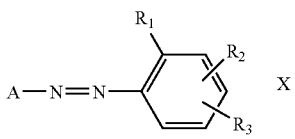 (I)

wherein:

A is chosen from one of the following heterocycles:

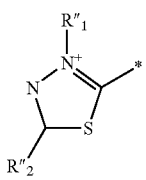 (1)

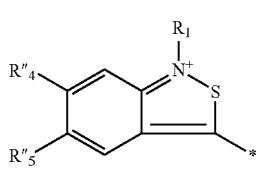 (2)

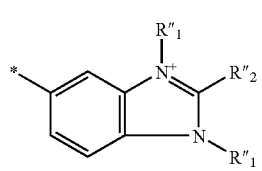 (3)

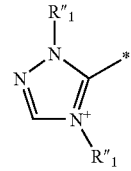 (4)

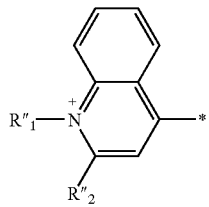 (5)

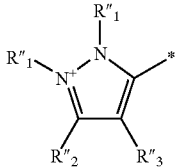 (6)

wherein:

in heterocycles (1)-(5), $R''_1$ is chosen from:
   $C_1$-$C_6$ alkyl radicals optionally substituted by at least one group chosen from hydroxyl groups: cyano groups, aminocarbonyl groups, and phenyl groups:

in heterocycle (6), $R''_1$ is chosen from:
   $C_1$-$C_6$ alkyl radicals substituted by at least one group chosen from hydroxyl groups; cyano groups, aminocarbonyl groups and phenyl groups;

in heterocycles (1)-(6), $R''_2$, $R''_3$, which may be identical or different, are chosen from:
   hydrogen;
   linear and branched $C_1$-$C_6$ alkyl groups;
   phenyl groups;
   amino groups optionally bearing one or two radicals which may be identical or different, chosen from:
      linear and branched $C_1$-$C_6$ alkyl radicals optionally substituted by a hydroxyl group or cyano group; and
      $C_5$-$C_7$ cyclic radicals;
   phenyl radicals;
   tetrahydro-1,1-dioxido-3-thienyl groups;

wherein the two alkyl radicals of the amino group may form, with the nitrogen atom to which they are attached, a 5- to 7-membered heterocycle optionally containing another heteroatom different or not different from nitrogen;

alkoxy ($C_1$-$C_6$) carbonyl groups;

in heterocycles (1)-(6), $R''_4$, $R_5$, which may be identical or different, are chosen from:
  hydrogen;
  linear and branched $C_1$-$C_6$ alkyl groups;
  linear and branched $C_1$-$C_6$ alkoxy groups;
  halogen atoms; and
  nitro groups;

in heterocycles (1)-(6), $R_1$ is chosen from:
  —NH—CO—$R'_1$ wherein $R'_1$ is chosen from:
    linear and branched $C_1$-$C_6$ alkyl radicals, optionally bearing a trialkyl ($C_1$-$C_4$) ammonium group or optionally bearing a phenoxy group;
    amino groups optionally bearing at least one group, which may be identical or different, chosen from $C_1$-$C_4$ alkyl, $C_1$-$C_4$ hydroxyalkyl, and phenyl groups;
  —NH—$SO_2$—$R'_2$ wherein $R'_2$ is chosen from linear and branched $C_1$-$C_6$ alkyl radicals;

in heterocycles (1)-(6), $R_2$ is chosen from:
  hydrogen,
  $C_1$-$C_6$ alkoxy groups;
  amino groups bearing one or two substituents which may be identical or different, chosen from:
    linear and branched $C_1$-$C_6$ alkyl radicals, optionally substituted by at least one group chosen from hydroxyl groups; $C_1$-$C_4$ alkoxy groups; alkoxy($C_1$-$C_4$)carbonyl groups; acyl($C_2$-$C_4$)oxy groups; phenyl groups; cyano groups;
    the two alkyl radicals of said amino group may form, with the nitrogen atom to which they are attached, a 5-membered or 6-membered heterocycle, which may be saturated or unsaturated, optionally containing another heteroatom identical to or different from nitrogen, and optionally substituted by at least one $C_1$-$C_4$ alkyl radical;
  cyclic $C_5$-$C_7$ alkyl radicals;
  naphthyl radicals;
  5-membered and 6-membered nitrogen-containing heterocycle, optionally unsaturated, attached to the aromatic nucleus by means of a nitrogen atom, optionally containing another heteroatom chosen from nitrogen or oxygen, said heterocycle being optionally substituted by at least one radical chosen from linear and branched $C_1$-$C_4$ alkyl radicals;
  phenyl radicals optionally substituted by at least one entity chosen from $C_1$-$C_4$ alkoxy, $C_1$-$C_4$ hydroxyalkoxy, cyano, linear, branched and cyclic $C_1$-$C_6$ alkyl, hydroxyl, amino, amino substituted by one or two $C_1$-$C_4$ alkyl radicals which may be identical or different, alkyl($C_1$-$C_4$)carbonyl, acetylamino, aminocarbonyl, and carboxy groups, and halogen atoms;
  amino groups monosubstituted by a phenyl radical optionally bearing a linear or branched $C_1$-$C_4$ alkoxy group, substituted by a group —D—NH—φ($R_1$)($R_3$)—N=N—A wherein D is a group chosen from alkylene ($C_1$-$C_2$)-φ-, —NHCO-φ-, —O-alkylene ($C_1$-$C_2$)—O—φ-, and —NH—CO—NH—φ- groups, or a single bond; $R_1$, and A are as defined above and φ is a phenyl radical;

in heterocycles (1) -(6), $R_3$ is chosen from:
  hydrogen;
  linear and branched $C_1$-$C_6$ alkyl radicals;
  $C_1$-$C_6$ alkoxy groups;
  amino groups optionally bearing at least one group chosen from $C_1$-$C_4$ alkyl, $C_1$-$C_4$ hydroxyalkyl, and phenyl groups, which may be identical or different;

in heterocycles (1) -(6), when $R_2$ and $R_3$ represent two amino groups disubstituted by two alkyl radicals which may be identical or different, carried by two adjacent carbon atoms of the aromatic nucleus, said radicals $R_2$ and $R_3$ can then form, with the carbon atoms to which each is attached, a saturated 6-membered heterocycle optionally substituted by one or two $C_1$-$C_4$ alkyl radicals, linear or branched, which may be identical or different; and one of the carbon atoms of said heterocycle can be replaced by a carbonyl group;

* at least one of the two radicals $R_2$ or $R_3$ being different from hydrogen;

* X is a cosmetically acceptable anion or mixture of anions.

2. The cosmetic composition according to claim 1, wherein the at least one compound of formula (I) is such that $R_3$ is in the meta position relative to the azo functional group.

3. The cosmetic composition according to claim 1, wherein the at least one compound of formula (I) is such that $R_2$ is in the para position relative to the azo functional group.

4. The cosmetic composition according to claim 1, wherein the at least one compound of formula (I) is such that X is chosen from halides; hydroxides; sulphates; hydrogensulphates; alkyl(Ci-$C_6$)sulphates; phosphates; carbonates hydrogencarbonates; perchlorates; acetates; tartrates; citrates, oxalates; alkyl($C_1$- $C_6$) sulphates; arylsulphonates substituted or not by a $C_1$-$C_4$ alkyl radical.

5. The cosmetic composition according to claim 1, wherein the at least one compound of formula (I) is present in an amount ranging from 0.001 wt.% to 10 wt.%, relative to the weight of the composition.

6. The cosmetic composition according to claim 5, wherein the at least one compound of formula (I) is present in an amount ranging from 0.05 wt.% to 5 wt.%, relative to the weight of the composition.

7. The cosmetic composition according to claim 1, further comprising at least one additive chosen from surfactants; anionic, cationic, non-ionic, amphoteric, and zwitterionic polymers; inorganic thickeners; polymeric thickeners; antioxidants; penetrants; sequestering agents; perfumes; buffers; dispersants; conditioners; film-forming agents; ceramides; preservatives; andopacifiers.

8. The cosmetic compostion according to claim 1, further comprising at least one cationic or non-ionic direct dye different from the at least one compound of formula (I).

9. The cosmetic composition according to claim 8, further comprising at least one oxidation base optionally together with at least one coupling agent.

10. A cosmetic composition for dyeing human keratin fibers, comprising, in a cosmetically acceptable medium, at least one dye chosen from compounds of formula (I), and mesomeric forms thereof:

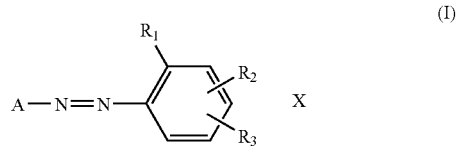

wherein:
A is chosen from one of the following heterocycles:

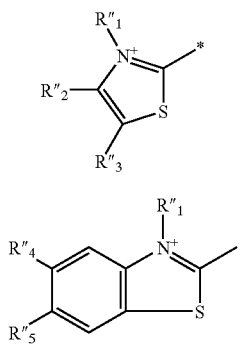

(8)

(9)

wherein:
in heterocycle (8), R″₁ is chosen from:
$C_1$-$C_6$ alkyl radicals optionally substituted by at least one group chosen from hydroxyl groups; cyano groups, aminocarbonyl groups, and phenyl groups;
R″₂, R″₃, which may be identical or different, are chosen from:
hydrogen;
linear and branched $C_1$-$C_6$ alkyl groups;
phenyl groups;
amino groups optionally bearing one or two radicals which may be identical or different, chosen from:
linear and branched $C_1$-$C_6$ alkyl radicals optionally substituted by a hydroxyl group or cyano group; and $C_5$-$C_7$ cyclic radicals;
phenyl radicals;
tetrahydro-1,1-dioxido-3-thienyl groups;
wherein the two alkyl radicals of the amino group may form, with the nitrogen atom to which they are attached, a 5- to 7- membered heterocycle optionally containing another heteroatom different or not different from nitrogen;
alkoxy($C_1$-$C_6$)carbonyl groups;
$R_1$ is chosen from: —NH—CO—R'₁ wherein R'₁ is chosen from:
linear and branched $C_1$-$C_6$ alkyl radicals, optionally bearing a trialkyl ($C_1$-$C_4$) ammonium group or optionally bearing a phenoxy group;
amino groups optionally bearing at least one group, which may be identical or different, chosen from $C_1$-$C_4$ alkyl, $C_1$-$C_4$ hydroxyalkyl, and phenyl groups;
—NH—SO₂—R'₂ wherein R'₂ is chosen from linear and branched $C_1$-$C_6$ alkyl radicals;
$R_2$ is chosen from:
hydrogen,
$C_1$-$C_6$ alkoxy groups;
amino groups bearing one or two substituents which may be identical or different, chosen from:
linear and branched $C_1$-$C_6$ alkyl radicals, optionally substituted by at least one group chosen from hydroxyl groups; $C_1$-$C_4$ alkoxy groups; alkoxy($C_1$-$C_4$)carbonyl groups; acyl($C_2$-$C_4$)oxy groups; phenyl groups; cyano groups;
the two alkyl radicals of said amino group may form, with the nitrogen atom to which they are attached, a 5-membered or 6-membered heterocycle, which may be saturated or unsaturated, optionally containing another heteroatom identical to or different from nitrogen, and optionally substituted by at least one $C_1$-$C_4$ alkyl radical;
cyclic $C_5$-$C_7$ alkyl radicals;
naphthyl radicals;
5-membered and 6-membered nitrogen-containing heterocycle, optionally unsaturated, attached to the aromatic nucleus by means of a nitrogen atom, optionally containing another heteroatom chosen from nitrogen or oxygen, said heterocycle being optionally substituted by at least one radical chosen from linear and branched $C_1$-$C_4$ alkyl radicals;
phenyl radicals optionally substituted by at least one entity chosen from $C_1$-$C_4$ alkoxy, $C_1$-$C_4$ hydroxyalkoxy, cyano, linear, branched and cyclic $C_1$-$C_6$ alkyl, hydroxyl, amino, amino substituted by one or two $C_1$-$C_4$ alkyl radicals which may be identical or different, alkyl($C_1$-$C_4$)carbonyl, acetylamino, aminocarbonyl, and carboxy groups, and halogen atoms;
amino groups monosubstituted by a phenyl radical optionally bearing a linear or branched $C_1$-$C_4$ alkoxy group, substituted by a group -D—NH—φ($R_1$)($R_3$)—N=N—A wherein D is a group chosen from -alkylene($C_1$-$C_2$)-φ-, —NHCO—φ, —O—alkylene ($C_1$-$C_2$)—O—φ-, and —NH—CO—NH—φ- groups, or a single bond; $R_1$, and A are as defined above and φ is a phenyl radical;
$R_3$ is chosen from:
hydrogen;
linear and branched $C_1$-$C_6$ alkyl radicals;
$C_1$-$C_6$ alkoxy groups;
amino groups optionally bearing at least one group chosen from $C_1$-$C_4$ alkyl, $C_1$-$C_4$ hydroxyalkyl, and phenyl groups, which may be identical or different;
when $R_2$ and $R_3$ represent two amino groups disubstituted by two alkyl radicals which may be identical or different, carried by two adjacent carbon atoms of the aromatic nucleus, said radicals $R_2$ and $R_3$ can then form, with the carbon atoms to which each is attached, a saturated 6-membered heterocycle optionally substituted by one or two $C_1$-$C_4$ alkyl radicals, linear or branched, which may be identical or different; and one of the carbon atoms of said heterocycle can be replaced by a carbonyl group;
\* at least one of the two radicals $R_2$ or $R_3$ being different from hydrogen;
\* X is a cosmetically acceptable anion or mixture of anions; and
in heterocycle (9), R″₁ is chosen from:
$C_1$-$C_6$ alkyl radicals optionally substituted by at least one group chosen from hydroxyl groups; cyano groups, aminocarbonyl groups, and phenyl groups;
R″₄, R″₅, which may be identical or different, are chosen from:
hydrogen;
linear or branched $C_1$-$C_6$ alkyl groups;
linear or branched $C_1$-$C_6$ alkoxy group;
halogen atoms;
nitro groups;
$R_1$ is chosen from
—NH—CO—R'₁ wherein R'₁ is chosen from:
linear and branched $C_1$-$C_6$ alkyl radicals, optionally bearing a trialkyl ($C_1$-$C_4$) ammonium groups or optionally bearing a phenoxy group;
amino groups optionally bearing at least one group, which may be identical or different, chosen from $C_1$-$C_4$ alkyl, $C_1$-$C_4$ hydroxyalkyl, and phenyl groups;

—NH—SO$_2$—R'$_2$ wherein R'$_2$ is chosen from linear and branched C$_1$-C$_6$ alkyl radicals;

R$_2$ is chosen from:
  hydrogen,
  C$_1$-C$_6$ alkoxy groups;
  amino groups bearing one or two substituents which may be identical or different, chosen from:
    linear and branched C$_1$-C$_6$ alkyl radicals, optionally substituted by at least one group chosen from hydroxyl groups; C$_1$-C$_4$ alkoxy groups; alkoxy(C$_1$-C$_4$)carbonyl groups; acyl(C$_2$-C$_4$)oxy groups; phenyl groups; cyano groups;
    the two alkly radicals of said amino group may form, with the nitrogen atom to which they are attached, a 5-membered or 6-membered heterocycle, which may be saturated or unsaturated, optionally containing another heteroatom identical to or different from nitrogen, and optionally substituted by at least one C$_1$-C$_4$ alkyl radical;
  cyclic C$_5$-C$_7$ alkyl radicals;
  naphthyl radicals;
  5-membered and 6-membered nitrogen-containing heterocycle, optionally unsaturated, attached to the aromatic nucleus by means of a nitrogen atom, optionally containing another heteroatom chosen from nitrogen or oxygen, said heterocycle being optionally substituted by at least one radical chosen from linear and branched C$_1$-C$_4$ alkyl radicals;
  phenyl radicals optionally substituted by at least one entity chosen from C$_1$-C$_4$ alkoxy, C$_1$-C$_4$ hydroxyalkyl, cyano, linear, branched and cyclic C$_1$-C$_6$ alkyl, hydroxyl, amino, amino substituted by one or two C$_1$-C$_4$ alkyl radicals which may be identical or different, alkyl(C$_1$-C$_4$)carbonyl, acetylamino, aminocarbonyl, and carboxy groups, and halogen atoms;
  amino groups monosubstituted by a phenyl radical optionally bearing a linear or branched C$_1$-C$_4$ alkoxy group, substituted by a group —D—NH—φ(R$_1$)(R$_3$)—N=N—A wherein D is a group chosen from -alkylene(C$_1$-C$_2$)-φ-, —NHCO—φ-, —O—alkylene(C$_1$-C$_2$)—O—φ-, and —NH—CO—NH—φ-, groups, or a single bond; R$_1$, and A are as defined above and φ is a phenyl radical;

R$_3$ is chosen from:
  hydrogen;
  linear and branched C$_1$-C$_6$ alkyl radicals;
  C$_1$-C$_6$ alkoxy groups;
  amino groups optionally bearing at least one group chosen from C$_1$-C$_4$ alkyl, C$_1$-C$_4$ hydroxyalkyl, and phenyl groups, which may be identical or different;
when R$_2$ and R$_3$ represent two amino groups disubstituted by two alkyl radicals which may be identical or different, carried by two adjacent carbon atoms of the aromatic nucleus, said radicals R$_2$ and R$_3$ can then form, with the carbon atoms to which each is attached, a saturated 6-membered heterocycle optionally substituted by one or two C$_1$-C$_4$ alkyl radicals, linear or branched, which may be identical or different; and one of the carbon atoms of said heterocycle can be replaced by a carbonyl by a carbonyl group;
with the proviso that when R$_1$ is —NH—CO—R'$_1$ and R'$_1$ is methyl, then R$_2$ is hydrogen and R$_3$ is NR$_{10}$R$_{11}$ in the para-position where:

R$_{10}$ is a linear or branched C$_1$-C$_6$ alkyl radical;

R$_{11}$ is a linear or branched C$_1$-C$_6$ alkyl radical substituted by at least one group chosen from alkoxy(C$_1$-C$_4$)carbonyl groups; acyl(C$_2$-C$_4$)oxy groups; phenyl groups; cyano groups;

* at least one of the two radicals R$_2$ or R$_3$ being different from hydrogen; and

* X is a cosmetically acceptable anion or mixture of anions.

11. A cosmetic composition according to claim 10, wherein the compounds of formula (I) are chosen from:

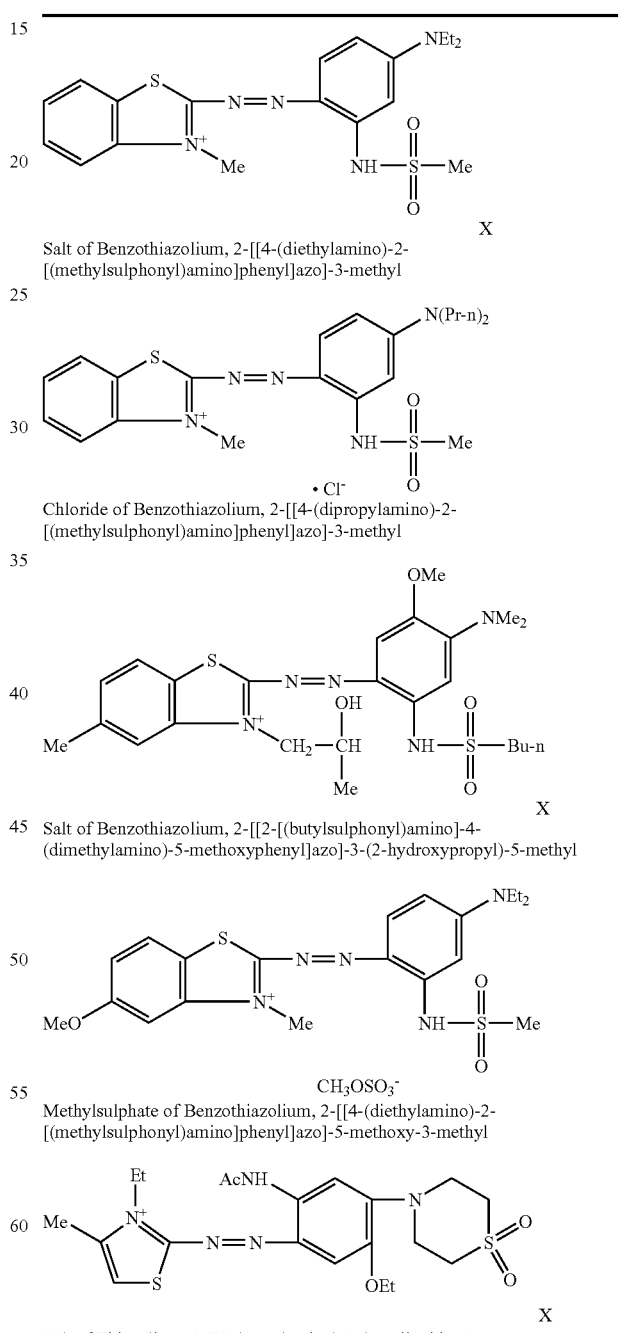

Salt of Benzothiazolium, 2-[[4-(diethylamino)-2-[(methylsulphonyl)amino]phenyl]azo]-3-methyl Chloride of Benzothiazolium, 2-[[4-(dipropylamino)-2-[(methylsulphonyl)amino]phenyl]azo]-3-methyl Salt of Benzothiazolium, 2-[[2-[(butylsulphonyl)amino]-4-(dimethylamino)-5-methoxyphenyl]azo]-3-(2-hydroxypropyl)-5-methyl Methylsulphate of Benzothiazolium, 2-[[4-(diethylamino)-2-[(methylsulphonyl)amino]phenyl]azo]-5-methoxy-3-methyl Salt of Thiazolium, 2-[[2-(acetylamino)-4-(1,1-dioxido-4-thiomorpholinyl)-5-ethoxyphenyl]azo]-3-ethyl-4-methyl -continued

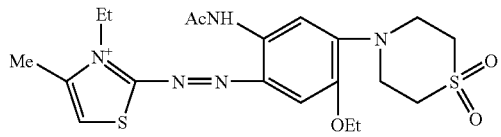

C₂H₅OSO₃⁻

Ethylsulphate of Thiazolium, 2-[(2-acetamido-5-ethoxy-4-thiomorpholinophenyl)azo]-3-ethyl-4-methyl-S,S-dioxide

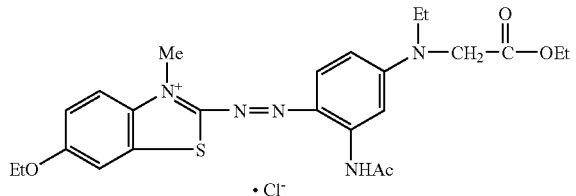

• Cl⁻

Chloride of Benzothiazolium, 2-[[2-(acetylamino)-4-[(2-ethoxy-2-oxoethyl)ethylamino]phenyl]azo]-6-ethoxy-3-methyl

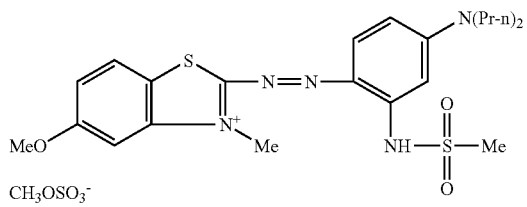

CH₃OSO₃⁻

Methylsulphate of Benzothiazolium, 2-[[4-(dipropylamino)-2-[(methylsulphonyl)amino]phenyl]azo]-5-methoxy-3-methyl

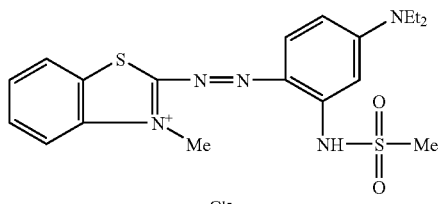

• Cl⁻

Chloride of Benzothiazolium, 2-[[4-(diethylamino)-2-[(methylsulphonyl)amino]phenyl]azo]-3-methyl

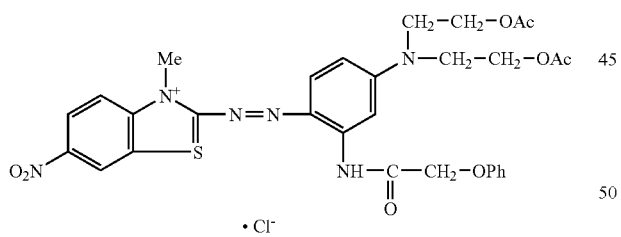

• Cl⁻

Chloride of Benzothiazolium, 2-[[4-[bis(2-hydroxyethyl)amino]-2-(2-phenoxyacetamido)phenyl]azo]-3-methyl-6-nitro

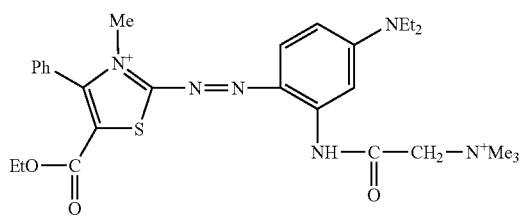

X

Salt of Thiazolium, 2-[[4-(diethylamino)-2-[[(trimethylammonio)acetyl]amino]phenyl]-azo]-5-(ethoxycarbonyl)-3-methyl-4-phenyl 12. A method of dyeing of keratin fibers comprising applying to the keratin fibers, which may be wet or dry, at least one cosmetic dye composition, for a sufficient length of time to obtain the desired effect, wherein the at least one cosmetic dye composition comprises, in a cosmetically acceptable medium, at least one dye chosen from compounds of formula (I), and mesomeric forms thereof:

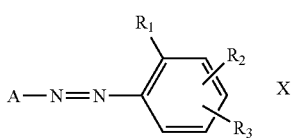

(I)

wherein:

A is chosen from one of the followinci heterocycles:

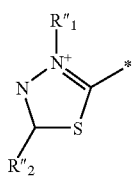

(1)

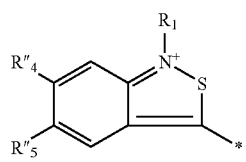

(2)

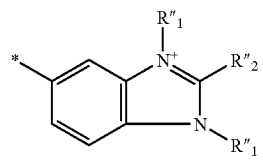

(3)

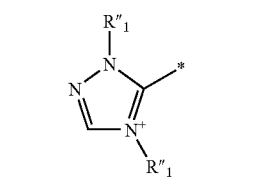

(4)

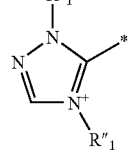

(5)

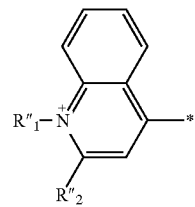

(6)

wherein:
in heterocycles (1)-(5), $R''_1$ is chosen from:
- $C_1$-$C_6$ alkyl radicals optionally substituted by at least one group chosen from hydroxyl groups; cyano groups, aminocarbonyl groups, and phenyl groups;

in heterocycle (6), $R''_1$ is chosen from:
- $C_1$-$C_6$ alkyl radicals substituted by at least one group chosen from hydroxyl groups;
  cyano groups, aminocarbonyl groups and phenyl groups; in heterocycles (1)-(6), $R''_2$, $R''_3$, which may be identical or different, are chosen from:
- hydrogen:
- linear and branched $C_1$-$C_6$ alkyl groups;
- phenyl groups;
- amino groups optionally bearing one or two radicals which may be identical or different, chosen from:
  - linear and branched $C_1$-$C_6$ alkyl radicals optionally substituted by a hydroxyl group or cyano group: and $C_5$-$C_7$ cyclic radicals;
  - phenyl radicals;
  - tetrahydro-1,1-dioxido-3-thienyl groups;
  - wherein the two alkyl radicals of the amino group may form, with the nitrogen atom to which they are attached, a 5- to 7-membered heterocycle optionally containing another heteroatom different or not different from nitrogen;
- alkoxy($C_1$-$C_6$)carbonyl groups;

in heterocycles (1)-(6), $R''_4$, $R''_5$, which may be identical or different, are chosen from:
- hydrogen:
- linear and branched $C_1$-$C_6$ alkyl groups;
- linear and branched $C_1$-$C_6$ alkoxy groups;
- halogen atoms; and
- nitro groups: in heterocycles (1)-(6) R1 is chosen from:
  —NH—CO—$R'_1$ wherein $R'_1$ is chosen from:
  - linear and branched $C_1$-$C_6$ alkyl radicals, optionally bearing a trialkyl ($C_1$-$C_4$) ammonium group or optionally bearing a phenoxy group;
  - amino groups optionally bearing at least one group, which may be identical or different, chosen from $C_1$-$C_4$ alkyl, $C_1$-$C_4$ hydroxyalkyl, and phenyl groups;
  —NH—SOhd 2—$R'_2$ wherein $R'_2$ is chosen from linear and branched $C_1$-$C_6$ alkyl radicals;

in heterocycles (1)-(6), $R_2$ is chosen from:
- hydrogen,
- $C_1$-$C_6$ alkoxy groups;
- amino groups bearing one or two substituents which may be identical or different, chosen from:
  - linear and branched $C_1$-$C_6$ alkyl radicals, optionally substituted by at least one group chosen from hydroxyl groups; $C_1$-$C_4$ alkoxy groups; alkoxy($C_1$-$C_4$)carbonyl groups; acyl($C_2$-$C_4$)oxy groups; phenyl groups; cyano groups;
  - the two alkyl radicals of said amino group may form, with the nitrogen atom to which they are attached, a 5-membered or 6-membered heterocycle, which may be saturated or unsaturated, optionally containing another heteroatom identical to or different from nitrogen, and optionally substituted by at least one $C_{1-4}$ alkyl radical;
- cyclic $C_5$-$C_7$ alkyl radicals;
- naphthyl radicals;
- 5-membered and 6-membered nitrogen-containing heterocycle, optionally unsaturated, attached to the aromatic nucleus by means of a nitrogen atom, optionally containing another heteroatom chosen from nitrogen or oxygen, said heterocycle being optionally substituted by at least one radical chosen from linear and branched $C_1$-$C_4$ alkyl radicals;
- phenyl radicals optionally substituted by at least one entity chosen from $C_1$-$C_4$ alkoxy, $C_1$-$C_4$ hydroxyalkoxy, cyano, linear, branched and cyclic $C_{01}$-$C_6$ alkyl, hydroxyl, amino, amino substituted by one or two $C_1$-$C_4$ alkyl radicals which may be identical or different, alkyl($C_1$-$C_4$carbonyl, acetylamino, aminocarbonyl, and carboxy groups, and halogen atoms;
- amino groups monosubstituted by a phenyl radical optionally bearing a linear or branched $C_1$-$C_4$ alkoxy group, substituted by a group —D—NH—φ($R_1$($R_3$)—N═N—A wherein D is a group chosen from -alkylene ($C_1C_2$)- φ-, —NHCO—φ-, —O-alkylene ($C_1$-$C_2$)—O—φ-, and —NH—CO—NH—φ- groups, or a single bond; $R_1$, and A are as defined above and 1 is a phenyl radical;

in heterocycles (1)-(6), R3 is chosen from:
- hydrogen;
- linear and branched $C_1$-$C_6$ alkyl radicals;
- $C_1$-$C_6$ alkoxy groups;
- amino groups optionally bearing at least one group chosen from $C_1$-$C_4$ alkyl, $C_1$-$C_4$ hydroxyalkyl, and phenyl groups, which may be identical or different;

in heterocycles (1)-(6), when R2 and K represent two amino groups disubstituted by two alkyl radicals which may be identical or different, carried by two adjacent carbon atoms of the aromatic nucleus, said radicals $R_2$ and $R_3$ can then form, with the carbon atoms to which each is attached, a saturated 6-membered heterocycle optionally substituted by one or two $C_1$-$C_4$ alkyl radicals, linear or branched, which may be identical or different; and one of the carbon atoms of said heterocycle can be replaced by a carbonyl group;

* at least one of the two radicals K or R3 being different from hydrogen;

* X is a cosmetically acceptable anion or mixture of anions.

13. The method according to claim 12, wherein the composition further comprises at least one additional direct dye different from the at least one compound of formula (I), and at least one oxidation base, optionally together with at least one coupling agent.

14. The method according to claim 13, wherein the at least one additional direct dye is a cationic or non-ionic dye, chosen from nitrobenzene dyes, azo, azomethine, methine, tetraazapenthamethine, anthraquinone, naphthoquinone, benzoquinone, phenothiazine indigo, xanthene, phenanthridine, phthalocyanine dyes, dyes derived from triarylmethane, and natural dyes.

15. The method according to claim 12, wherein the composition further comprises at least one oxidizing agent.

* * * * *

UNITED STATES PATENT AND TRADEMARK OFFICE
CERTIFICATE OF CORRECTION

PATENT NO. : 7,497,878 B2  Page 1 of 4
APPLICATION NO. : 11/477381
DATED : March 3, 2009
INVENTOR(S) : Lagrange It is certified that error appears in the above-identified patent and that said Letters Patent is hereby corrected as shown below:

On the title page, Item (57), lines 8-9, "as a dyeing" should read --as dyeing--.

Col. 30, line 55,

"
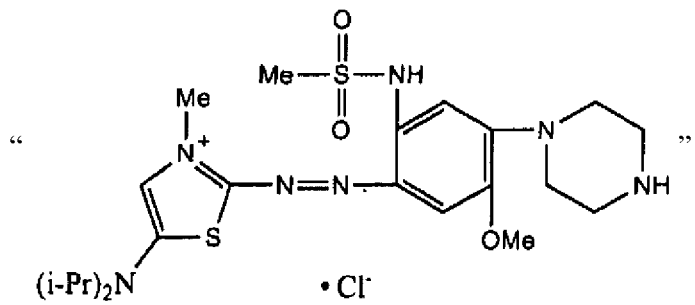
"

should read:

--
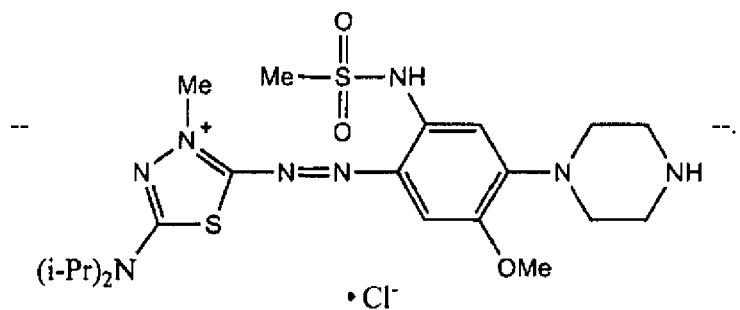
--.

In the claims:

Claim 1, column 44, line 49, "groups:" should read --groups,--.

Claim 1, column 44, line 50, "groups:" should read --groups;--.

Claim 1, column 44, line 52, "$C_1$-$C_6$alkyl" should read --$C_1$-$C_6$ alkyl--.

Claim 1, column 45, line 6, "alkoxy ($C_1$-$C_6$) carbonyl" should read --alkoxy($C_1$-$C_6$)carbonyl--.

Claim 1, column 45, lines 59-60, "-D-NH-ɸ($R_1$)($R_3$)-N=N-A" should read -- -D-NH-Φ($R_1$)($R_3$)-N=N-A--.

UNITED STATES PATENT AND TRADEMARK OFFICE
CERTIFICATE OF CORRECTION

PATENT NO. : 7,497,878 B2
APPLICATION NO. : 11/477381
DATED : March 3, 2009
INVENTOR(S) : Lagrange It is certified that error appears in the above-identified patent and that said Letters Patent is hereby corrected as shown below:

Claim 1, column 45, lines 60-62, "alkylene ($C_1$-$C_2$)-ɸ-, -NHCO-ɸ-, -O-alkylene ($C_1$-$C_2$)-O-ɸ-, and -NH-CO-NH-ɸ-" should read --alkylene($C_1$-$C_2$)-Φ-, -NHCO-Φ-, -O-alkylene ($C_1$-$C_2$)-O-Φ-, and -NH-CO-NH-Φ- --.

Claim 1, column 45, line 63, "and ɸ is" should read --and Φ is--.

Claim 4, column 46, line 27, "alkyl(Ci-$C_6$)sulphates;" should read --alkyl($C_1$-$C_6$)sulphates;--.

Claim 4, column 46, line 27, "carbonates" should read --carbonates;--.

Claim 4, column 46, line 29, "alkyl($C_1$-$C_6$) sulphates;" should read --alkyl($C_1$-$C_6$)sulphonates;--.

Claim 7, column 46, line 46, "andopacifiers." should read --and opacifiers.--.

Claim 10, column 47, line 39, "5 - to" should read --5- to--.

Claim 10, column 48, lines 23-24, "-D-NH-ɸ($R_1$)($R_3$)-N=N-A" should read -- -D-NH-Φ($R_1$)($R_3$)-N=N-A--.

Claim 10, column 48, lines 24-26, "-alkylene($C_1$-$C_2$)-ɸ-, -NHCO-ɸ, -O-alkylene ($C_1$-$C_2$)-O-ɸ-, and -NH-CO-NH-ɸ-" should read -- -alkylene($C_1$-$C_2$)-Φ-, -NHCO-Φ-, -O-alkylene ($C_1$-$C_2$)-O-Φ-, and -NH-CO-NH-Φ- --.

Claim 10, column 48, line 27, "and ɸ is" should read --and Φ is--.

Claim 10, column 49, lines 42-43, "-D-NH-ɸ($R_1$) ($R_3$)-N=N-A" should read -- -D-NH-Φ($R_1$)($R_3$)-N=N-A--.

Claim 10, column 49, lines 44-45, "-alkylene($C_1$-$C_2$)-ɸ-, -NHCO-ɸ-, -O-alkylene ($C_1$-$C_2$)-O-ɸ-, and -NH-CO-NH-ɸ-," should read -- -alkylene($C_1$-$C_2$)-Φ-, -NHCO-Φ-, -O-alkylene ($C_1$-$C_2$)-O-Φ-, and -NH-CO-NH-Φ- --.

Claim 10, column 49, line 47, "and ɸ is" should read --and Φ is--.

UNITED STATES PATENT AND TRADEMARK OFFICE
CERTIFICATE OF CORRECTION

PATENT NO. : 7,497,878 B2
APPLICATION NO. : 11/477381
DATED : March 3, 2009
INVENTOR(S) : Lagrange It is certified that error appears in the above-identified patent and that said Letters Patent is hereby corrected as shown below:

Claim 10, column 49, line 65, "-NH-CO-R'$_1$ and" should read -- -NH-CO-R'$_1$, and--.

Claim 12, column 52, line 1, "dyeing of keratin" should read --dyeing keratin--.

Claim 12, column 52, line 20, "followinci" should read --following--.

Claim 12, column 53, line 12, "hydrogen:" should read --hydrogen;--.

Claim 12, column 53, line 17, "C$_1$C$_6$" should read --C$_1$-C$_6$--.

Claim 12, column 53, line 18, "group:" should read --group;--.

Claim 12, column 53, line 21, "tetrahydro- 1,1-dioxido-3-thienyl" should read --tetrahydro-1,1-dioxido-3-thienyl--.

Claim 12, column 53, line 30, "hydrogen:" should read --hydrogen;--.

Claim 12, column 53, line 34, "groups:" should read --groups;--.

Claim 12, column 53, line 34, "R1" should read --R$_1$--.

Claim 12, column 53, line 42, "-NH-SOhd 2-R'$_2$" should read -- -NH-SO$_2$-R'$_2$--.

Claim 12, column 53, line 60, "C$_1$-$_4$" should read --C$_1$-C$_4$--.

Claim 12, column 54, line 12, "C$_{01}$-C$_6$" should read --C$_1$-C$_6$--.

Claim 12, column 54, line 15, "alkyl(C$_1$-C$_4$carbonyl," should read --alkyl(C$_1$-C$_4$)carbonyl,--.

Claim 12, column 54, lines 19-20, "-D-NH-φ(R$_1$(R$_3$)-N=N-A" should read -- -D-NH-Φ(R$_1$)(R$_3$)-N=N-A--.

Claim 12, column 54, lines 20-22, "-alkylene (C$_1$C$_2$)- φ-, -NHCO-φ-, -O-alkylene (C$_1$-C$_2$)-O-φ-, and -NH-CO-NH-φ-" should read -- -alkylene(C$_1$-C$_2$)-Φ-, -NHCO-Φ-, -O-alkylene (C$_1$-C$_2$)-O-Φ-, and -NH-CO-NH-Φ- --.

UNITED STATES PATENT AND TRADEMARK OFFICE
CERTIFICATE OF CORRECTION

| | |
|---|---|
| PATENT NO. | : 7,497,878 B2 |
| APPLICATION NO. | : 11/477381 |
| DATED | : March 3, 2009 |
| INVENTOR(S) | : Lagrange |

It is certified that error appears in the above-identified patent and that said Letters Patent is hereby corrected as shown below:

Claim 12, column 54, line 23, "and 1 is" should read --and $\Phi$ is--.

Claim 12, column 54, line 25, "R3" should read --$R_3$--.

Claim 12, column 54, line 32, "R2 and K" should read --$R_2$ and $R_3$--.

Claim 12, column 54, line 35, "R$_3$can" should read --$R_3$ can--.

Claim 12, column 54, line 41, "K and R3" should read --$R_2$ and $R_3$--.

Signed and Sealed this

Second Day of June, 2009

JOHN DOLL
*Acting Director of the United States Patent and Trademark Office*